US008043855B2

(12) United States Patent
Armendariz Borunda et al.

(10) Patent No.: US 8,043,855 B2
(45) Date of Patent: *Oct. 25, 2011

(54) RECOMBINANT ADENOVIRAL VECTORS AND THEIR UTILITY IN THE TREATMENT OF VARIOUS TYPES OF FIBROSIS: HEPATIC, RENAL, PULMONARY, AS WELL AS HYPERTROPHIC SCARS

(75) Inventors: Juan Armendariz Borunda, Col. Prado Coapa (MX); Estuardo Aguilar Cordova, Col. Prado Coapa (MX)

(73) Assignee: TGT Laboratories, S.A. DE C.V., Col. Prado Coapa (MX)

( * ) Notice: Subject to any disclaimer, the term of this patent is extended or adjusted under 35 U.S.C. 154(b) by 36 days.

This patent is subject to a terminal disclaimer.

(21) Appl. No.: 10/724,292

(22) Filed: Dec. 1, 2003

(65) Prior Publication Data

US 2004/0156827 A1    Aug. 12, 2004

Related U.S. Application Data

(60) Division of application No. 10/098,359, filed on Mar. 18, 2002, now abandoned, which is a continuation of application No. PCT/MX00/00035, filed on Sep. 14, 2000.

(30) Foreign Application Priority Data

Sep. 17, 1999  (MX) .................. PA/A/1999/008515

(51) Int. Cl.
*C12N 15/63* (2006.01)
*C12N 15/00* (2006.01)
*C07H 21/04* (2006.01)

(52) U.S. Cl. ............... 435/455; 435/320.1; 536/23.5; 536/24.1

(58) Field of Classification Search ............... 514/44; 435/320.1, 455; 424/93.2, 93.21; 536/23.5, 536/24.1
See application file for complete search history.

(56) References Cited

U.S. PATENT DOCUMENTS

| | | | |
|---|---|---|---|
| 5,166,320 A | 11/1992 | Wu et al. ................. 530/395 |
| 5,240,846 A | 8/1993 | Collins et al. ............. 435/240.1 |
| 5,521,291 A | 5/1996 | Curiel et al. ............ 530/391.7 |
| 5,547,932 A | 8/1996 | Curiel et al. ................ 435/65 |
| 5,559,099 A | 9/1996 | Wickham et al. ............... 514/44 |
| 5,585,362 A | 12/1996 | Wilson et al. ................ 514/44 |
| 5,670,488 A | 9/1997 | Gregory et al. ............... 514/44 |
| 5,712,136 A | 1/1998 | Wickham et al. .......... 435/172.3 |
| 5,756,086 A | 5/1998 | McClelland et al. ........ 424/93.2 |
| 5,770,442 A | 6/1998 | Wickham et al. .......... 435/320.1 |
| 5,827,703 A | 10/1998 | Debs et al. ............... 435/172.3 |
| 5,846,782 A | 12/1998 | Wickham et al. ............ 435/697 |
| 5,856,152 A | 1/1999 | Wilson et al. ............ 435/172.3 |
| 5,871,982 A | 2/1999 | Wilson et al. |
| 5,872,154 A | 2/1999 | Wilson et al. ................ 514/885 |
| 5,885,808 A | 3/1999 | Spooner et al. ............ 435/172.3 |
| 5,895,759 A | 4/1999 | Strauss et al. .............. 435/320.1 |
| 5,910,487 A | 6/1999 | Yew et al. ................... 514/44 |
| 5,922,576 A | 7/1999 | He et al. |
| 5,980,886 A * | 11/1999 | Kay et al. ................ 424/93.21 |
| 6,265,212 B1 | 7/2001 | Fallaux et al. |
| 6,436,393 B1 * | 8/2002 | Bilbao et al. .............. 424/93.2 |
| 6,686,198 B1 * | 2/2004 | Melton et al. ................ 435/377 |

FOREIGN PATENT DOCUMENTS

| | | |
|---|---|---|
| WO | WO 96/18419 | 6/1996 |
| WO | WO 97/17090 | 5/1997 |
| WO | WO 98/48024 | 10/1998 |

OTHER PUBLICATIONS

Deonarain, M.,1998, Expert Opin. Ther. Pat., vol. 8, pp. 53-69.*
Verma, et al., Sep. 1997, Nature, vol. 389, pp. 239-242.*
Eck et al., 1996, Goodman & Gilman's The Pharmacological Basis of Therapeutics, McGraw-Hill, New York, p. 77-101.*
Gorecki, 2001, Expert Opin. Emerging Drugs, 6(2): 187-198.*
Rudinger, 1976, Peptide Hormones, Edited by Parsons, University Park Press, Baltimore, p. 1-7.*
Kaye et al., 1990, Proc. Natl. Acad. Sci. USA, vol. 87, pp. 6922-6926.*
Davis, C. G., 1990, The New Biologist, vol. 2, No. 5, p. 410-419.*
Skolnick et al., 2000, Trends in Biotech, vol. 18, p. 34-39.*
Hattori et al., Jan. 1999, Human Gene Therapy, vol. 10, No. 2, pp. 215-222.*
Jaffe et al., Apr.-May 1999, Experimental Lung Research, vol. 25, No. 3, pp. 199-215.*
Li et al., Aug. 1998, Gene Therapy, vol. 5, p. 1105-1113.*
Varga et al., 2007, The Journal of Clinical Investigation, vol. 117, No. 3, p. 557-567.*
Fernandez et al., 1998, Surgery, vol. 124, p. 129-136.*
Hasty et al., 1990, The Journal of Biological Chemistry, vol. 265, No. 20, pp. 11421-11424.*
Baker et al., 1996, Matrix Biology, vol. 15, pp. 383-395.*
Brinckerhoff et al., 1987, Journal of Clinical Investigation, vol. 79, p. 542-546.*
Devarajan et al., 1992, The Journal of Biological Chemistry, vol. 267, No. 35, p. 25228-25232.*

(Continued)

*Primary Examiner* — Shin-Lin Chen

(74) *Attorney, Agent, or Firm* — Morgan, Lewis & Bockius LLP

(57) ABSTRACT

The invention encompasses the use of gene therapy for the treatment of different kinds of fibrosis in human beings. Specifically, the invention encompasses the use of therapeutic genes specifically directed to target organs to revert and/or prevent the development of the fibrosis process. The invention further encompasses genes encoding for proteins including human MMP-8 active and latent, MMP-1, MMP-2, MMP-9 and MMP-13; human uPA wild type and/or modified (or its truncated version), the truncated receptor for TGF-β type II and Smad-7, which can be directed by adenovirus and/or other recombinant vectors that cannot transduce (i.e., infect) others organs. The gene therapy of the invention further encompasses treating disorders including renal fibrosis, pulmonary fibrosis, hypertrophic and keloid scars (i.e., skin fibrosis), and other kinds of fibrosis.

1 Claim, 12 Drawing Sheets

OTHER PUBLICATIONS

Freije et al., 1994, Journal of Biological Chemistry, vol. 269, No. 24, p. 16766-16773.*

Tomasinsig et al., 2005, Current Protein and Peptide Science, vol. 6, p. 23-34.*

Smallwood et al., 2002, Virology, vol. 304, p. 135-145.*

Chattopadhyay et al., 2004, Virus Research, vol. 99, p. 139-145.*

P. P. Anthony, K. G. Hishack, N. C. Nayak, H. E. Poulsen, P. J. Scheuer, L. H. Sobin; "The Morphology of Cirrhosis: Definition, Nomenclature and Classification", *Bulletin of the World Health Organization*; 1977; 55:521-540.

J. Armendariz-Borunda and M. Rojkind; "A Simple Quantitative Method for Collagen Typing in Tissue Samples: Its Application to Human Liver with Schistosomiasis"; *Collagen Rel. Res.* 1984, vol. 4, 35-47.

J. Armendariz-Borunda, K. Katayama and J. M. Seyer; "Transcriptional Mechanisms of Type I Collagen Gene Expression are Differentially Regulated by Interleukin-1β, Tumor Necrosis Factor α, and Transforming Growth Factor β in Ito Cells"; *J. Biol. Chem.* 267:14316-14321; 1992.

J. Armendariz-Borunda, H. Katai, C. M. Jones, J. M. Seyer, A. H. Kang, and R. Raghow; "Transforming Growth Factor β Gene Expression is Transiently Enhanced at a Critical Stage during Liver Regeneration Following $CCl_4$ Treatment"; *Laboratory Investigation*; 69:283-294, 1993.

J. Armendariz-Borunda, C. Simkevich, N. Roy, R. Raghow, A. H. Kang and J. M. Seyer, "Activation of Ito Cells Involves Regulation of AP-1 Collagen Gene Expression"; *Biochemical Journal* 304:817-824, 1994.

C. Chen and H. Okayama; "Calcium Phosphate-Mediated Gene Transfer: a Highly Efficient Transfection System for Stably Transforming Cells with Plasmidic DNA", *Biotechniques* 1988, 6:632-638.

J.T. Douglas and D. T. Curiel, "Adenoviruses as Vectors for Gene Therapy", *Science and Medicine*, Mar./Apr. 1997, 44-53.

R. Dumaswala, D. Berkowitz and J. E. Heubi, "Adaptive Response of the Enterohepatic Circulation of Bile Acids to Extrahepatic Cholestiasis", *Hepatology* 1996, vol. 23, No. 3: 623-629.

Scott L. Friedman, "The Cellular Basis of Hepatic Fibrosis: Mechanisms and Treatment Strategies", *The New England Journal of Medicine* 1993, vol. 328, No. 25:1828-1835.

F.L. Graham and A. J. Van Der Eb, "A New Technique for the Assay of Infectivity of Human Adenovirus 5 DNA", *Virology* 1973, 52:456-467.

Tong-Chuan He, Shibin Zhou, Luis T. Da Costa, Kian Yu, Kenneth W. Kinzler and Bert Vogelstein, "A Simplified System for Generating Recombinant Adenoviruses", *Proc. Natl. Acad. Sci. USA*, vol. 95: 2509-2514, Mar. 1998.

S. Lee, C. Girod, A. Draillon, A. Hadengue, and D. Lebec, "Hemodynamic Characterization of Chronic Bile Duct-Ligated Rats: Effect of Pentobarbital Sodium", *AM Journal Fisiol.* 1986; 251:176-180.

Marie-Jeanne T. F. D. Vrancken Peeters, A. Lieber, J. Perkins, and M. A. Kay; "Methods for Multiple Portal Vein Infusion in Mice: Quantitation of Adenovirus-Mediated Hepatic Gene Transfer"; *BioTechniques* Feb. 1996; 20:278-285.

D. Martinez-Fong, J. E. Mullersman, A. F. Purchio, J. Armendariz-Borunda, and A. Martinez-Hernandez, "Nonenzymatic Glycosylation of Poly-L-lysine: A New Tool for Targeted Gene Delivery", *Hepatology*, vol. 20, No. 6: 1602-1608.

F. Mion, A. Geloen, E. Agosto and Y. Minaire, "Carbon Tetrachloride Induced Cirrhosis in Rats: Influence of the Acute Effects of the Toxin on Glucose Metabolism", *Hepatology* 1996 vol. 23, No. 2:582-587.

S. Nakano, J. Haratake, and H. Hashimoto, "Alteration in Bile Ducts and Peribiliary Microcirculation in Rats After Common Bile Duct Ligation"; *Hepatology*, 1995, vol. 21, No. 5, 1380-1386.

J. L. Poo, A. Estanes, J. Pedraza-Chaverri, C. Cruz, C. Perez, A. Huberman and M. Uribe; "Cronologia de Hipertension Portal, Disminucion de Excrecion de sodio y activacion del sistema renina-angiotensina en cirrosis biliar experimental", Rev., *Invest Clin.*, 49:15-23, 1997.

A. Rojas-Martinez, P. R. Wyde, C. A. Montgomery, S. H. Chen, S. L. C. Woo, and E. Auilar-Cordova; "Distribution, Persistency, Toxicity and Lack of Replication of an E1A-Deficient Adenoviral Vector after Intracardiac Delivery in the Cotton Rat"; *Cancer Gene Ther.*, vol. 5, 1998, pp. 365-370.

S. Shimohama, M. B. Rosenberg, A. M. Fagan, J. A. Wolff, M. P. Short, X. O. Breakefield, T. Friedmann, and F. H. Gage, "Grafting Genetically Modified Cells into the Rat Brain: Characteristics of *E. Coli* β-Galactosidase as a Reporter Gene"; *Molecular Brain Res.* 5:271-278; 1989.

D. J. Weiss, D. Liggitt and J. G. Clark, "In Situ Histochemical Detection of β-Galactosidase Activity in Lung: Assessment of X-Gal Reagent in Distinguished *lacZ* Gene Expression and Endogenous β-Galactosidase Activty", *Human Gene Therapy*, Sep. 1, 1997; 8:1545-1554.

M. A. Zern and T. F. Kresina, "Hepatic Drug Delivery and Gene Therapy", *Hepatology*, 1997, vol. 25, No. 2, 484-491.

G. Zhu, A. G. Nicolson, X. Zheng, T. B. Strom and V.P. Sukhatme; "Adenovirus-Mediated β-Galactosidase Gene Delivery to the Liver Leads to Protein Deposition in Kidney Glomeruli"; *Kidney International*; 1997, vol. 52, 992-999.

Lieber, et al.: "A Modified Urokinase Plasminogen Activator Induces Liver Regeneration Without Bleeding", Human Gene Therapy, vol. 6, pp. 1029-1037, 1995.

Salgado, et al.: "Liver Cirrhosis is Reverted by Urokinase-Type Plasminogen Activator Gene Therapy", Molecular Therapy, vol. 2(6), pp. 545-551, 2000.

Bramson, et al.: "The Use of Adenoviral Vectors for Gene Therapy and Gene Transfer In Vivo", Current Opinion in Biotechnology, vol. 6, pp. 590-595, 1995.

Weitzman: "Functions of the Adenovirus E4 Proteins and Their Impact on Viral Vectors", Frontiers in Bioscience, vol. 10, pp. 1106-1117, 2005.

Armendariz-Borunda, J. et al.: "Regulation of TGF Gene Expression in Rat Liver Intoxicated with Carbon Tetrachloride", FASEB J., 4: 215-221, 1990.

Arthur, M. J. P.: "Collagenases and Liver Fibrosis", J. Hepatology, 22: 43-48, 1995.

Bradford, M. M.: "A Rapid and Sensitive Method for the Quantification of Microgram Quantities of Protein Utilizing the Principle of Protein-Dye Binding", Anal. Biochem., 72: 248-254, 1976.

Brann, T. et al.: "Adenoviral Vector-Mediated Expression of Physiologic Levels of Human Factor Viii Nonhuman Primates", Hum. Gene Ther., 10: 2999-3011, 1999.

Carmeliet et al.: "Adenovirus-mediated transfer of tissue-type plasminogen activator augments thrombolysis in tissue-type plasminogen activator-deficient and plasminogen activator inhibitor-1 -overexpressing mice", Blood, 4: 1527-1534, 1997.

Corcoran, M. L. et al.: "MMP-2: Expression, Activation and Inhibition", Enzyme Protein, 49(1-3): 7-19, 1996.

Dai et al.: "Advances in Gene Therapy of Liver Cirrhosis: A Review", World J. Gastroenterol, 7(1): 1-8, 2001.

Delgado-Rizo, V. et al.: "Treatment with Anti-Transforming Grown Factor, Antibodies Influences and Altered Patter of Cytokines Gene Expression in Injured Rat Liver", Biochem. Biophys., Acta, 1442: 20-27, 1998.

Douglas, J. T. et al.: "Adenoviruses as Vectors for Gene Therapy", Science and Medicine, p. 44-53, 1997.

Foecking et al.: "Powerful and Versatile Enhancer-Promoter Unit for Mammalian Expression Vectors", Gene, 45(1): 101-105, 1986.

Gao, C. et al.: "Intramuscular of an Hepatic Transduction with a Retroviral Vector in Mice", Human Gene Ther., 10: 911-922,. 1999.

Garcia-Banuelos, J. et al.: "Adenovirus-Mediated Gene Delivery of Cirrhotic Rat Livers: Potential Tool for Gene Therapy", Gene Ther., 9: 127-134, 2000.

Gros et al.: "Regulated production of mature insulin by non-beta-cells", Human Gene Therapy, 8(18): 2249-2259, 1997.

Kim, T. H. et al.: "Extracellular Matrix Remodeling at the Early Stages of Liver Regeneration in the Rat", Hepatology, 26: 896-904, 1997.

Liu, M. L. et al.: "Collagenase Pretreatment and the Mitogenic Effects of Hepatocyte Growth Factor and Transforming Growth Factor-Alpha in Adult Rat Liver", Hepatology, 19: 1521-1522, 1994.

Liu, M. L. et al.: "Uptake and Distribution of Hepatocyte Growth Factor in Normal and Regenerating Adult Rat Liver", Am. J. Pathology, 144: 129-140, 1994.

Locaputo, S. et al.: "Regulation of Gene Expression During Liver Regeneration of Urokinase Transgenic Mice", Hepatology, 29: 1106-1113, 1999.

Ludin et al.: "Application of novel vectors for GFP-tagging of proteins to study microtubule-associated protein" Gene, 173: 107-111, 1996.

Mariani, S. et al.: "Knocking Out Alcohol Damage", Nature Med., 5(11): 1243, 1999.

Mars, W. M. et al.: "Activation of Hepatocyte Growth Factor by the Plasminogen Activators uPA and tPA", Am. J. Pathol., 143: 949-958, 1993.

Michalopoulos, G. K. et al.: "HGF in Liver Regeneration and Tumor Promotion", Prog. Clin. Biol. Res., 391: 179-195, 1995.

Michalopoulos, G. K. et al.: "Liver Regeneration", Science, 276: 60-66, 1997.

Nyberg-Hoffman, C. et al.: "Sensitivity and Reproductibility in Adenoviral Infectious Titer Determination", Nature Med., 3(7): 808-811, 1997.

Olaso, E. et al.: "Molecular Regulation of Hepatic Fibrogenesis", J. Hepatology, 29: 836-847, 1998.

Oxford Textbook of Clinical Hepatology, 1: 371-390, 1991.

Roselli, H. T. et al.: "Liver Regeneration is Transiently Impaired in Urokinase-Deficient Mice", Am. J. Physiol., 275: G14272-G14279, 1998.

Schirmacher, F. et al.: "The Role of Ito Cells in the Biosynthesis of HGF-SF in the Liver", EXS, 65: 285-299, 1993.

Steler-Stevenson, W. G.: "Dynamics of Matrix Turnover During Pathologic Remodeling of the Extracellular Matrix", Am. J. Pathol., 148: 1345-1350, 1996.

Thomas et al.: "Progress and problems with the use of viral vectors for gene therapy", Nature Reviews/Genetics, 4: 346-358, 2003.

Verheijen, J. M. et al.: "Modified Proenzymes as Artificial Substrates for Proteolytic Enzymes: Coloimetric Assay of Bacterial Collagenase and Matrix Metalloproteinase Activity Using Modified Pro-Urokinase", Biochem. J., 323: 603-609, 1997.

Wolf, H. K. et al.: "Localization of Hepatocyte Growth Factor in Human and Rat Tissues: An Immunohistochemical Study", Hepatology, p. 14488-14494, 1991.

\* cited by examiner

ADND

ADN - CaPO$_4$

GELR ADN -PL

ADN -PL

RECOMBINANT ADENOVIRAL VECTORS AND THEIR UTILITY IN THE TREATMENT OF VARIOUS TYPES OF FIBROSIS: HEPATIC, RENAL, PULMONARY, AS WELL AS HYPERTROPHIC SCARS

CROSS REFERENCE TO RELATED APPLICATIONS

This application is a divisional of U.S. application Ser. No. 10/098,359, filed Mar. 18, 2002, now abandoned, which is a continuation of the national stage designation of PCT/MX00/00035, filed Sep. 14, 2000, the disclosures of which are incorporated herein in their entirety.

TECHNICAL FIELD OF THE INVENTION

The present invention relates to the creation of RECOMBINANT ADENOVIRAL vectors bearing exogenous genes that encode for therapeutic proteins useful in the treatment of HEPATIC cirrhosis and generalized FIBROSIS, such as renal FIBROSIS, pulmonary FIBROSIS, HYPERTROPHIC scars and keloid of the skin, and/or in other target organs susceptible to suffer from it. It also relates to a mechanism of tissue-specific recognition of the affected cells by means of delivery of therapeutic genes to cirrhotic organs.

Moreover, the invention provides an effective way for the treatment of fibrosis through the employment of recombinant adenoviral vectors which are claimed here, as well as the process to prepare these vectors, the pharmaceutical composition that contains them, and their therapeutic uses in the treatment of several fibrosis, which has great commercial expectancy in the pharmaceutical industry and also presents an important alternative as gene therapy for the treatment of chronic-degenerative diseases characterized by fibrosis, with great therapeutic application in the field of Medicine.

INTRODUCTION

Physiopathology of Hepatic Cirrhosis

Hepatic cirrhosis is a disease resulting from hepatic chronic damage. Damage might be toxic (chronic ingestion of alcohol), infectious (viral hepatitis, mainly by hepatitis B and/or C virus), immunological, (primary biliary cirrhosis), by biliary obstruction, (secondary biliary cirrhosis), metabolic (Wilson's disease). All forms of cirrhosis have characteristics in common: synthesis and excessive deposition of proteins of extracellular matrix (ECM), (mainly collagen I and to a lesser extent collagens IV and III), and consequently the formation of nodules of hepatocytes, abnormal vascularization and portal hypertension (Antoni P P, Ishak K G, Nayak N C, Poulsen H E, Scheuer P J, Sobin L H. The morphology of cirrhosis: definition, nomenclature, and classification. Bulletin of the World Health Organization. 1977; 55:521-540 y Scott L. Friedman The cellular basis of hepatic fibrosis: Mechanisms and treatment strategies. The New England Journal of Medicine 1993, vol. 328 No. 25:1828-1835). These physiopathological processes lead to an alteration in the blood supply and in consequence in the nutrition of hepatic cells. Regardless of the ethiological agent and morphologic differences, all forms of cirrhosis have as a common end, hepatic failure causing the patient's death.

As a consequence of the excessive deposition of collagen proteins in the sub-endothelial space of the sinusoids (Space of Disse), various changes occur in the hepatic microenvironment: loss of hepatocyte villi, formation of a basement membrane composed by collagens IV and I covering the sinusoids, and loss of the fenestration of endothelial cells which forms the sinusoids. All this process is known as "capillarization" of the sinusoids. (Scott L. Friedman The cellular basis of hepatic fibrosis: Mechanisms and treatment strategies. The New England Journal of Medicine 1993, vol. 328 No. 25:1828-1835). Thus, the liver is not able to maintain the physiologic concentration of solutes in the terminal hepatic vein, in other words, HEPATIC failure sets in. This capillarization, with the formation of the continuous endothelia (collagen of basement membrane) and the accumulation of other collagenic proteins, represents a barrier to the normal and bi-directional exchange of molecules between the plasma and hepatocytes, as can be appreciated in FIG. 1, where hepatic cirrhosis is characterized by the accumulation in the liver of type I collagen. With an excessive deposition of this protein, the free exchange of nutrients between blood and liver cells is impeded, the inactivation of toxic agents by this organ can not be carried out, becoming this the main cause of the pathophysiology of the disease. To date, no therapeutic agent that could revert and/or prevent with a 100% effectiveness the progressive accumulation of hepatic collagen has been described.

Such physiopathological alterations presented in hepatic cirrhosis are constant and common for the organs that also undergo fibrosis, such as, lung, heart, kidney, skin, among others, which should be not considered as limitations of the scope of protection of this invention. Therefore, the methodology presented here for the treatment of hepatic cirrhosis could be applied also to those organs that are susceptible to, or are affected by fibrosis.

Viral Vectors and Hepatic Gene Therapy

This technology can be implemented with viral or non-viral vectors. Previous studies have been designed using plasmids and liposomes (DOTMA), cationic and anionic, etc. Among the methods employing viral vectors, the most commonly used include the use of retrovirus and adenovirus.

In a number of protocols, retroviral vectors have been used to introduce genes in hepatocytes (JT, and Curiel D T, Adenoviruses as Vectors for gene Therapy. Science and Medicine/1997 44-53). However, precautions have to be taken since these vectors can generate potential replication-competent viruses. Among the advantages of these vectors is their ability to integrate their genome in a stable way in the chromosomes of the guest cell, which confers the possibility of expression, in an indefinite way, of the therapeutic transgene cloned in the retrovirus. On the other hand, up to date, no study has reported incidences of mutagenesis by insertion or activation of oncogenes by the incorporation of the replication-deficient retrovirus. Nevertheless, the use of retroviral vectors to transduce genes to the liver is limited for the following considerations: 1) these vectors infect only cells which actively divide and 2) very low viral particles titers are obtained in the packing cell lines used to amplify these viruses (Graham F L, and Van Der Eb A J. A New Technique for the Assay of Infectivity of Human Adenovirus 5 DNA. Virology 1973, 52:456-467). These two limitations have been successfully overcome in other Gene Therapy protocols through the induction of hepatocytes proliferation "in vivo", through the use Hepatic Growth Factors and through partial hepatectomy, surgical procedure by which the removal of 70% of liver mass induces division of the remaining hepatic cells "in vivo". The use of Lentiviral vectors has permitted to overcome partially said limitations, because they are able to transduce cells which are not actually dividing.

BACKGROUND OF THE INVENTION

Hepatic cirrhosis is a chronic illness of the liver, where diffuse cell necrosis and a limited regeneration of parenchymal hepatic cells result in diffuse percentage increase of connective tissue, causing the distortion of lobular hepatic architecture and inducing hemodynamic alterations. Therefore, some strategies for the treatment of hepatic cirrhosis could include the prevention and/or reversion of the "fibrogenic process", stimulation of hepatic mitosis and re-arrangement of the architecture of hepatic tissue. The documents of the state of the art related to the present invention are mentioned hereinafter only as references.

U.S. Pat. No. 5,240,846 refers to the use of gene therapy called "CFTR", which induces a stable correction of the regulation of the chlorine channel. This defect is present in epithelial cells. In said invention, adenoviral recombinant vectors are used as well as plasmidic vectors. However, it does not have any association with the therapeutics genes of the present invention. Likewise, U.S. Pat. No. 5,910,487, describes the use of plasmidic vectors for sending therapeutic molecules, but there is no association with the delivery of genes of metalloproteases MMP-8 latent and/or active, MMP-1, MMP-2, MMP-9, MMP-13; or "uPA (wild type uPA and/or its modified versions) or "Smad7" or the truncated receptors for transforming growth factor-$\beta$ (TGF-$\beta$ type II) as presented here. U.S. Pat. No. 5,827,703 refers to the use of adenoviral vector and modified adenoviral vector to send genes, however none of these vectors contain the genes used in the present invention for the treatment of fibrosis.

U.S. Pat. No. 5,770,442 claims the use of a recombinant adenovirus that contains one gene directing the expression of a protein called "fiber" or a protein called "Fiber-chimera", however said patent does not specifically mention, which one is the therapeutic gene. Also, a method of gene therapy involving the use of such adenovirus and a vector of transference for the generation of such recombinant adenovirus is presented. However, nothing is mentioned with regard to the use of therapeutic genes cloned and inserted in recombinant adenoviral vectors used in this invention in fibrotic livers, or to other target organs such as kidney, lung, and hypertrophic scars and others. These therapeutic genes are the gene that codes for human metalloproteases MMP-8, latent and/or active, MMP-1, MMP-2, MMP-9 and MMP-13; human urokinase Plasminogen Activator (wild type and/or modified huPA), Smad7, and the truncated receptor for TGF-$\beta$ type II, claimed herein. Other members of the family of genes represented are also included.

U.S. Pat. No. 5,166,320 refers to the use of a targeted delivery system to introduce exogenous genes in mammalian hepatic cells. But there is no association with putative genes directly sent to cirrhotic livers or to fibrotic kidney or lungs.

U.S. Pat. No. 5,872,154, describes a method to reduce the immune response induced by an adenoviral recombinant vector and a selected immune modulator, which functions by inhibiting the formation of neutralizing antibodies and/or reducing the death of the virally infected cells.

U.S. Pat. No. 5,871,982, is directed to a hybrid vector, in which a portion of an adenovirus is included, together with a portion of an adeno-associated viral vector that contains a selected transgene. A hybrid virus consisting of the union of a conjugate with a polycation to a gene mesh of the adeno-associated viral vector to form a simple particle is also described. This is contrary to the present invention in which no hybrid viruses are employed, only adenoviral vectors. Besides, in the above-mentioned patent the gene, transgene or therapeutic gene used is not stated.

U.S. Pat. No. 5,856,152 is directed to the creation of a hybrid vector which contains the portion of an adenoviral vector in combination with an adeno-associated virus and a selected gene. Thorough it large quantities of recombinant vectors are produced, but they are not carrying cloned therapeutic genes as is described in this invention, in which specific therapeutic genes for the treatment of renal and hepatic fibrosis and hypertrophic scars are used.

U.S. Pat. No. 5,547,932 claims a compound of complexes of nucleic acids for transfecting eucaryotic cells. These complexes are formed by nucleic acids and another substance with affinity for nucleic acids and optionally an internalizing factor, such as a virus or a component of the virus that can be conjugated. It also uses components of specific adenoviral vectors or specific viruses such as Ad2 or Ad5, but does not mention the genes that are internalized in the cell cytoplasm and eventually in the nucleus of these eucaryotic cells. Similarly, U.S. Pat. No. 5,521,291, is related to conjugated adenovirus bound through an antibody to a substance with affinity to nucleic acids. In this way recombinant genes are transported to the interior of eucaryotic cells. These conjugated complexes and nucleic acids are internalized in the cell, but the genes that can be sent are not specifically mentioned. In said patent, contrary to what is described in the instant invention, the use of such adenovirus to treat fibrosis or hepatic cirrhosis or any another type of fibrosis is not mentioned.

U.S. Pat. No. 5,585,362, relates to an improved adenoviral vector and methods to obtain and use such vectors. The use of adenoviral vectors is not mentioned in said patent. However the adenoviral vectors described in the present invention were used like vectors for sending therapeutic genes.

U.S. Pat. No. 5,756,086, claims an adenovirus, which is represented by a protein called "fiber", the adenovirus also includes a ligand, that is specific for a receptor located in a specific cell type. This adenovirus can have at least a portion of this protein called "fiber" and it can be removed and replaced with a ligand, which is specific for a receptor in specific cells of the economy, such as hepatocytes. This adenovirus can include a gene that codes for a therapeutic agent. Based on the previous statement, the outstanding technical difference of the instant invention compared to the state of the art, is the specificity of the therapeutic agent as human metalloproteases MMP-8 active and latent, MMP-1, MMP-2, MMP-9 and MMP-13; human uPA (urokinase Plasminogen Activator, wild type and/or modified), the truncated receptor for TGF-$\beta$ type II and "Smad7" for the treatment of various fibrosis.

U.S. Pat. No. 5,895,759 claims a tissue-specific vector (liver) for gene therapy that can be used to send genes to a damaged liver. These vectors are chemically or enzyme coupled to a promoter and can also be coupled to an antibody packaged in a polypeptidic envelope. Besides, the vector or the virus to be assayed is the hepatitis B virus. Thus the sending of genes to damaged livers described in this patent makes use of a system completely different from the one of this invention, and there is no relation with the process of fibrosis or cirrhosis to be treated.

U.S. Pat. No. 5,559,099 describes an adenoviral recombinant vector that contains a chimeric protein from the adenovirus called pentona, which includes a non-pentona sequence and a therapeutic gene to develop a gene therapy method involving the use of such adenovirus, transference adenoviral vectors for the recombination of such adenoviral vectors containing a therapeutic gene.

U.S. Pat. No. 5,885,808 claims also the use of adenovirus with bonding molecules of adenovirus to different cells, the molecules of which have been modified, as in U.S. Pat. Nos. 5,846,782 and 5,712,136, in which adenoviral vectors are employed, which have been modified to contain different peptidic domains.

Finally, U.S. Pat. No. 5,670,488 relates to vectors for gene therapy, which are especially useful for cystic fibrosis and also mentions the development of methods for the use of these vectors. The possible relation of the instant invention to the mentioned state of the art refers to the use of adenoviral vectors, that can be modified, as well as the use of inducible promoters driving the expression of genes to be inserted in these adenoviral vectors. However, the technical characteristics of the present invention are focused on the specific use of therapeutic genes to treat fibrosis of different kinds: hepatic, renal and pulmonary fibrosis, as well as hypertrophic scars.

The importance of the present invention, contrary to the state of the art described in the above-mentioned documents, is based on the technical characteristics of the invention itself, as well as on the additional advantages derived from the same, which are described with more details below.

Adenoviral Vectors

In the instant invention, the use of adenoviral vectors was determined based on several considerations: 1) these vectors can be generated to very high titers of infectious particles per ml.: ($10^9$-$10^{10}$); 2) they infect a great variety of cells, however, when they are administered i.v., most of them are located in the hepatic organ; 3) they transfer efficiently genes to cells that are not dividing, and 4) they are seldom integrated in the guest genome, which avoids the risk of cellular transformation by insertional mutagenesis (Douglas J T, and Curiel D T. Adenoviruses as Vectors for gene Therapy. Science and medicine, March/April 1997. 44-53 and Zern A M, and Kresina T F. Hepatic Drug delivery and Gene Therapy. Hepatology 1997, Vol. 25, No. 2, 484-491).

Adenovirus are probably the most promising vehicles or vectors for the delivery of genes in the protocols of gene therapy in human beings, since they possess a unique attribute that provides them great stability when they are administered into the bloodstream. This specific characteristic permits them to be efficiently used in clinical trials with a comfortable i.v. administration for the patient. (Douglas J T, and Curiel D T. Adenoviruses as vectors for Gene Therapy. Science and Medicine, March/April, 1997, 44-53).

Adenoviruses are double stranded DNA viruses. They have an icosahaedric structure, infect a great variety of mammalian cell types, and support the ubiquitous expression of a specific receptor in the cell surface not yet identified. Its union to cells occurs by means of the protein component of the capside and the virus enters into the cell by receptor-mediated endocytosis.

More than 40 different human serotypes of adenovirus have been identified, of which type 2 (Ad2) and 5(Ad5) have been more extensively studied and, therefore, more widely used as vectors for gene therapy. A very important characteristic of these two Ad serotypes is that they have never been associated with malignant human processes.

The strategy for the creation of recombinant adenovirus is based on the organization of the adenoviral genome. The expression of the adenoviral genes occurs in two phases, early and late, that are defined by the time of replication of the adenoviral genome. The early genes encode themselves in 4 distinct transcriptional units: E1, E2 and E4 encode for essential regulatory proteins that induce the replication of the adenoviral DNA. The gene E3 is a non-essential gene. The products of the late genes include the main proteins of the capside, which are transcribed from a unique promoter. (Graham F L, and Van Der Eb A J. A new technique for the assay of infectivity of human adenovirus 5 DNA. Virology 1973, 52:456-467).

The recombinant adenoviruses are generated by introduction of the exogenous gene or sequence of DNA of interest in substitution of the adenoviral genome regions required for the replication of the virus. The adenoviral recombinant vectors present deletions in E1 and E3 genome regions. Recombinant adenovirus generation is conducted both through the replacement of E1 or E3 regions or through the insertion of the exogenous gene between the E4 region and the right extreme of the adenoviral genome. Vectors based on the insertion of the exogenous gen at the right extreme of the adenoviral genome or by the replacement of the E3 region maintain their replication capability. On the contrary, the substitution of early region E1 produces a faulty vector in its replication capability, that, therefore, can spread only in a cell line that supplies in "trans" the absent functions of the replaced adenoviral region, or in presence of a collaborator virus. Of these, the most commonly used as gene transference vectors are the replication-deficient adenovirus (Douglas J T, and Curiel D T. Adenoviruses as vectors for Gene Therapy. Science and Medicine, March/April, 1997, 44-53).

The creation of adenoviral vectors, as well as their application for the treatment of fibrosis, are shown in the examples described hereinafter.

OBJECTS OF THE INVENTION

Hereinafter, the objects and advantages derived from this invention are presented.

An object of the present invention is to provide a procedure to prepare recombinant adenoviral vectors pAdGFP-MMP-8, by means of the cloning of the reporter genes: lac-7 and GFP and the therapeutic gene of collagenase or metalloprotease MMP-8 in its latent and/or active forms.

Another object of the invention is to provide an adenoviral recombinant vector with an exogenous gene or DNA sequence of interest that encodes for therapeutic proteins useful in the treatment of the generalized fibrosis, in target organs susceptible to suffer from it. Such genes are, but are not limited to MMP-8 active and latent, MMP-1, MMP-2, MMP-9 and MMP-13; and uPA (wild type and/or modified).

Also, in the present invention, pharmaceutical compositions are provided which contain the recombinant adenoviral vectors in quantities therapeutically effective of viral particles for the treatment of generalized fibrosis; as well as their uses and therapeutic applications in the treatment of fibrosis.

An advantage of greater importance in the treatment of the generalized fibrosis, particularly of hepatic cirrhosis, is that the delivery of therapeutic genes is carried out through tissue-specific recognition by the way of administration employed.

Another advantage of the therapeutic uses of the invention, which is directed initially to revert hepatic cirrhosis, is the treatment of generalized fibrosis in other target organs susceptible to suffer from it, including, without limitation, the treatment of fibrosis in lung, heart, skin, kidney, among others, in mammalian animals, including human beings.

Another object is the design of a technology to send genes efficiently to livers of animals affected by cirrhosis that resemble two types of cirrhosis that usually affect human beings (Alcoholic cirrhosis and Primary Biliary Cirrhosis).

Another advantage resulting from the fibrosis treatment is that recombinant adenovirus does not induce lethal toxicity in none of the injected animals with the vectors.

Another objective of the invention allows us to discriminate the modification of the staining reaction with X-Gal between the endogenous tissue -galactosidase activity and the bacterial -galactosidase induced by the infectious action of the adenoviral vector. The use of the green fluorescent protein permits us to verify the in vivo transduction of different organs in rats to verify if the vector administration was appropriate, if the expression remains, and besides not killing the animals it is possible to conduct follow up observation after surgery.

Finally, all this evidence let us suggest that our system comprises an efficient vehicle to deliver therapeutic genes such as human metalloproteases MMP-8 active and latent; MMP-1, MMP-2, MMP-9 and MMP-13; collagenase which degrade the deposited collagen excess and/or genes which encode for promoters of hepatic regeneration such as human uPA (urokinase Plasminogen Activator, modified and wild type), Hepatocite Grow Factor (HGF); the truncated receptor for TGF-β type II and Smad 7 to livers of cirrhotic rats, with the purpose to re-establish normal liver functions or normal functions of other organs affected by the same pathology.

Thus, in the present invention a process of preparation is given, through which adenoviral recombinant vectors, pharmaceutical compounds and therapeutic uses for the fibrosis treatment, especially for the treatment of hepatic cirrhosis.

BRIEF DESCRIPTION OF THE DRAWINGS

Other particularities and advantages of this invention will be evident in the following detailed description of the preferred objects and embodiments, from the enclosed claims and from the drawings or shapes attached, in which:

DETAILED DESCRIPTION OF THE INVENTION

There are many reports showing that through systemic administration of recombinant adenoviral vectors (AdR) into healthy experiment animals, a specific homing and highly preferential tropism of these vectors into the liver is observed. Up to now, it was not known whether the AdR were able to transduce cirrhotic rat livers. As previously mentioned, hepatic cirrhosis is characterized by an increase of fibrosis in the entire liver parenchyma, mainly around the central and portal veins, creating a barrier which hampers the exchange of macromolecules between the sinusoid and the hepatocytes (Antoni P P, Hishack K G, Nayak N C, Poulsen H E, Scheuer P J, Sobin L H. The morphology of cirrhosis: Definition, nomenclature and classification. Bulletin of the World Health Organization. 1977; 55:521-540; and Scott L. Friedman: The cellular basis of hepatic fibrosis: Mechanisms and treatment strategies, The New England Journal of Medicine, 1993, Vol. 328, No. 25:1828-1835), and this protocol was designed to verify if even in presence of this barrier, the exogenous genes could be systemically delivered to the cirrhotic liver.

Therefore, our hypothesis is that AdRs containing LacZ and GFP (green fluorescent protein) reporter genes are capable of transducing livers of cirrhotic rats even if the lobular architecture of the liver is distorted.

Figure 1:
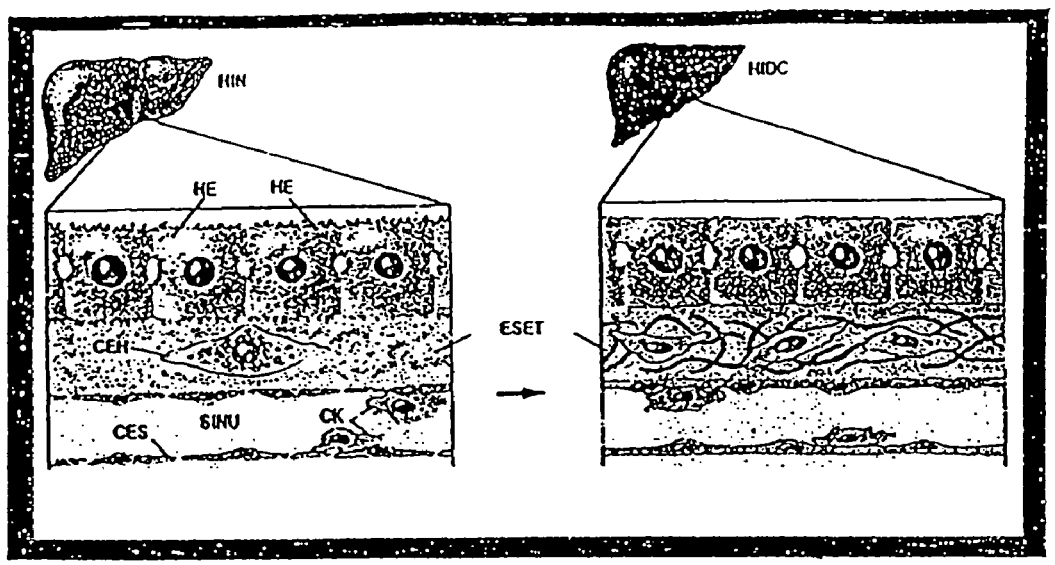
FIG. 1 shows the cellular physiopathology of hepatic cirrhosis.
Figure 2:
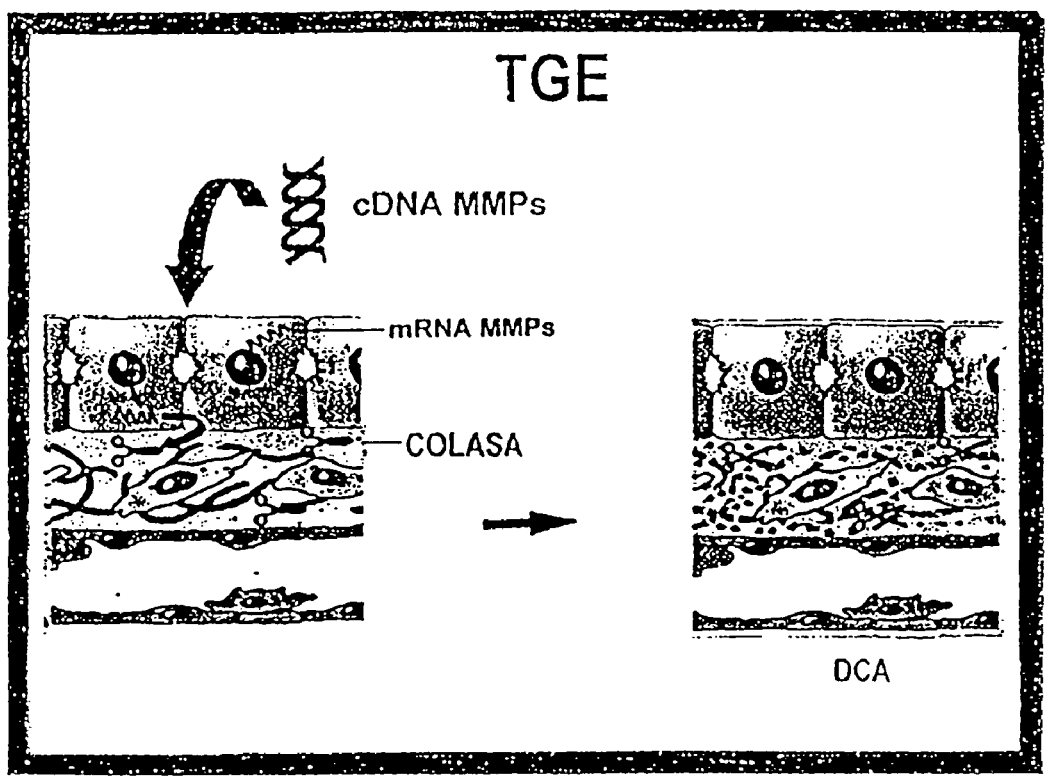
FIG. 2 shows the proof of concept on how gene therapy works by reverting the cirrhosis process.
Figure 18:
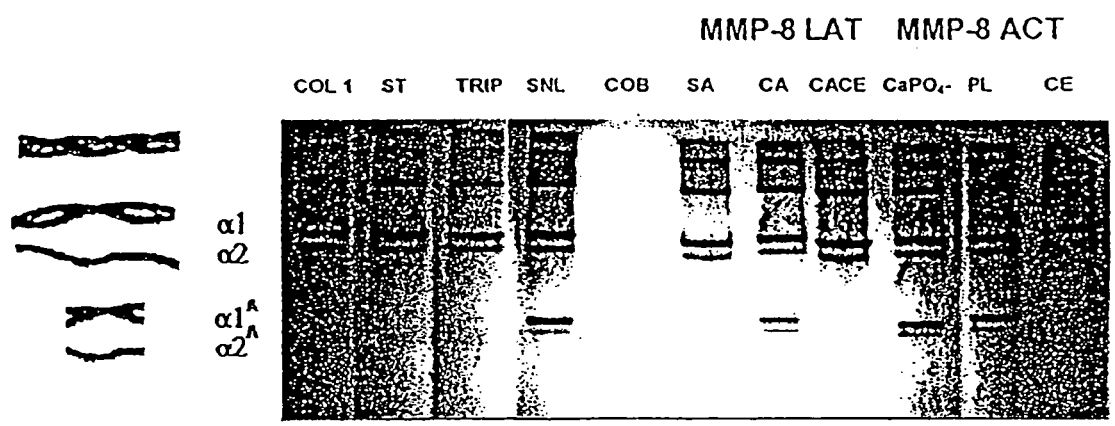
FIG. 18 shows analysis of the collagenolytic activity in the protein secreted to the culture medium by HepG2 cells after transfection with cDNAs for latent MMP-8 and active MMP-8.

Thus, we could sent to these livers therapeutic genes such as human metalloproteases or collagenases human MMP-8 active and latent, MMP-1, MMP-2, MMP-9 and MMP-3; human Urokinase Plasminogen Activator (uPA wild type and/or modified); the truncated receptor for TGF-β type II and Smad 7, which degrade the excess of collagenic proteins deposited and/or prevent the exacerbated synthesis of collagenic proteins, as it is shown in FIGS. 2 and 18; and/or genes which encode for proteins stimulating hepatic regeneration such as uPA, in order to re-establish the normal functioning of the liver, as is shown in FIG. 2.

The current invention initiates a research line to carry out gene therapy as an alternative for the treatment of chronic degenerative disease, specifically of hepatic cirrhosis in human beings, through the establishment of an efficient vehicle to send genes to the liver which will produce therapeutic proteins to help re-establish the normal functions of the liver, see FIG. 2. FIG. 2 shows how sending efficiently a therapeutic gene to the liver, in this case, a collagenase (metalloproteases of matrix, MMPs), it is possible to promote degradation of collagen through the over-expression of these metalloproteases.

Figure 3:
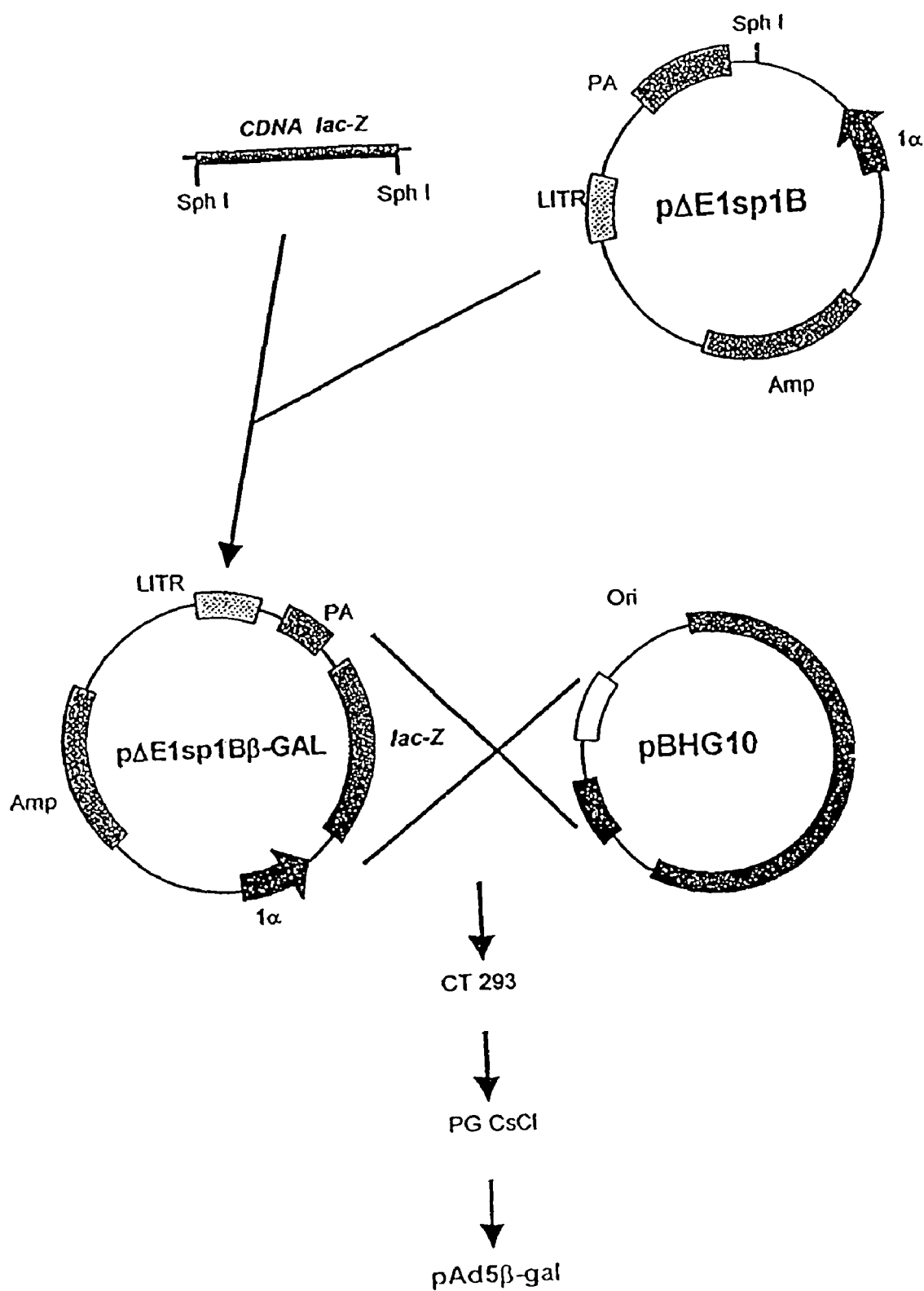
FIG. 3 is the schematic representation, which shows the cloning and production of the adenoviral vector Ad5-gal.
Figure 4:
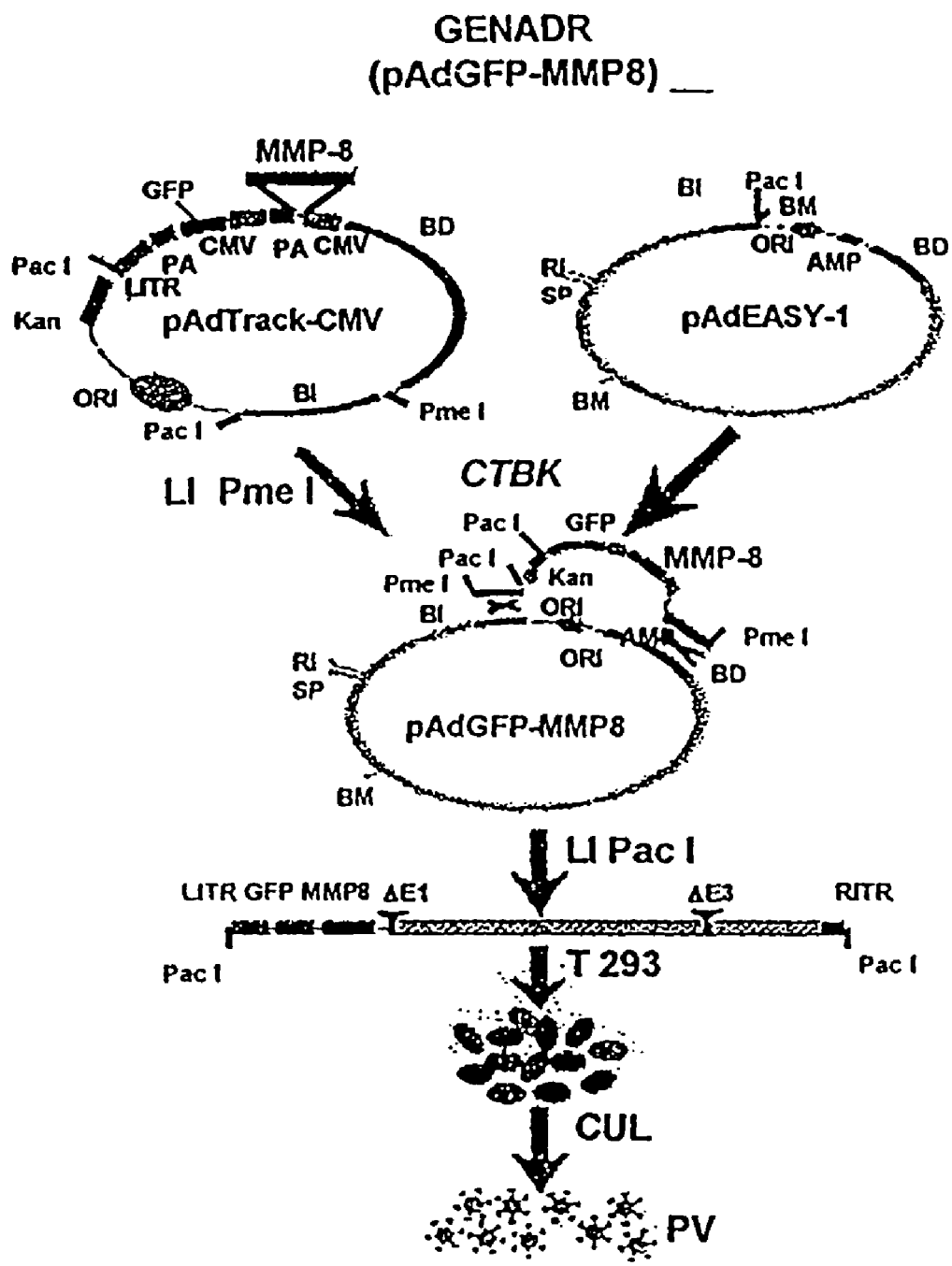
FIG. 4 shows the schematic development of the AdEasy system to generate recombinant adenoviruses, specifically the pAdGFP-MMP-8.
Figure 5:
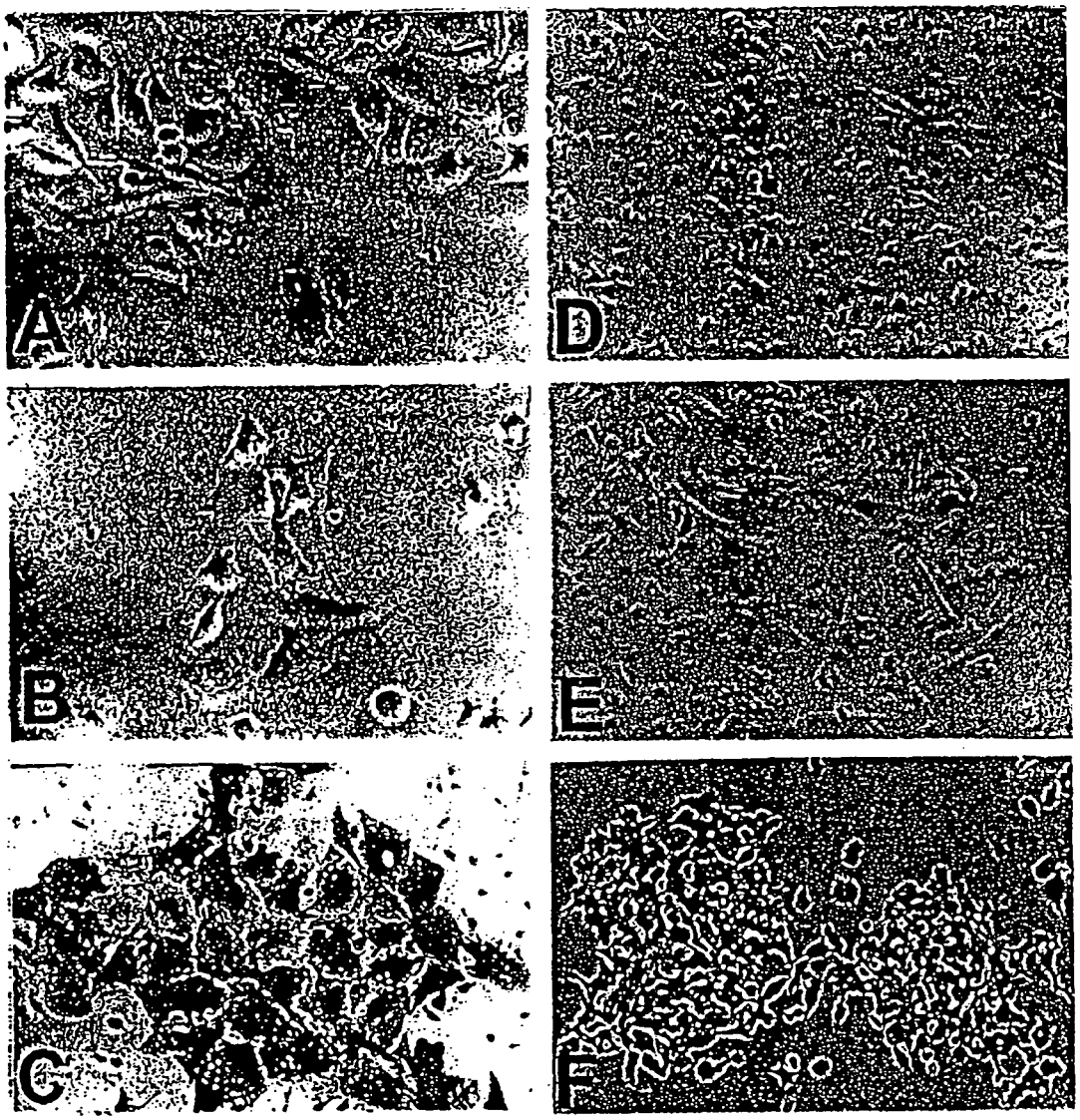
FIG. 5 shows the analysis of the expression of -galactosidase in cultured cells.

In FIG. 3, the strategy for the cloning and production of an adenoviral vector is shown. The plasmid pDeltaE1sp1B contains adenovirus Ad5 sequences, in which the bacterial gene Lac-z was inserted. This plasmid was recombined with the pBHG10 to obtain complete viral particles after co-transfection in the cell line 293. The vector pAdGFP was obtained as follows: the MMP-8 gene (coming from the plasmid PEPCK-MMP-8) was cloned in the vehicle vector, pAdTrack-CMV, the resultant plasmid is linearized with the restriction endonuclease Pme I, and is then transformed in E. coli (BJ5183) with the plasmid pAdEASY-1. The recombinant colonies were selected through kanamicine resistance, and the recombination is confirmed by restriction analysis with endonucleases. Finally, the recombinant plasmid linearized is transfected in the packaging cell line (293 cells), the recombinant adenoviruses are obtained within 7 to 12 days as illustrated in FIGS. 3 and 4 (Tong Chuan H., Shibin Z., Luis T. Jian Y, Kenneth W. and Volgestein Bert: A simplified system for generating recombinant adenoviruses. Prod. Natl. Acad. Sci. USA Vol. 95: 2509-2514, March 1998). To evaluate the grade of transduction in vitro liver HepG2 cell line and peritoneal macrophages isolated from mouse were used. In FIG. 5 the expression of -galactosidase in cultured cells is shown. A), B) and C) correspond to HepG2 cells (32O×); D), E) and F), are mouse peritoneal macrophages (100×). In C) and F) the transduced cells are shown with $1 \times 10^8$ viral particles/ml from the Ad5-Gal vector. Three techniques were conducted to compare the degree of incorporation of the reporter gene Lac-Z which was administered to each culture dish in the form of plasmidic DNA PGK-Gal, through precipitation with $Ca^{++}$ phosphate (Chen C, and Okayama H. Calcium Phosphate mediated gene transfer, a highly efficient system to establish transforming cells with plasmidic DNA. Biotechniques 1988, 6:632-638), DNA complexes-polylysine-Lactose (Martinez-Fong D., Mullersman J E, Purchio A F, Armendariz-Borunda J., and Martinez-Hernandez A., Non enzymatic glycosylation of poly-L-lysine: A new tool for targeted gene delivery. Hepatology, Vol. 20, No. 6: 1602-1608), with the vectors Ad5-gal and pAdGFP-MMP8. The visualization of the activity of Gal was verified with the reactive Xgal and the GFP in a microscope-stereoscope of fluorescence. For the in vivo assay, gal staining was standardized using different pHs of the suspension with the reactive Xgal (Weiss D J, Ligitt D., and Clark J G. In situ photochemical detection of galactosidase activity in lung: assessment of Xgal reagent in distinguished Lac-Z gene expression and endogenous galactosidase activity. Human being therapy, Sep. 1, 1997, 8:1545-1554).

The models of experimental hepatic cirrhosis used are: a) Chronic intoxication caused by carbon tetrachloride ($CCl_4$), in which hepatic cirrhosis is established starting from the $8^{th}$ week of peritoneal administration (Mion F, Geloen A, Agosto E. and Minaire Y. Carbon tetrachloride induced cirrhosis in rats: influence of the acute effects of the toxin on glucose metabolism. Hepatology 1996, Vol. 23, No. 2:582-587); and B), ligation of the bile duct (LCB) in which cirrhosis is observed after the fourth week of surgery (Lee S, Giraud C., Draillon A., HADengue A., and Lebec D., Hemodynamic characterization of chronic bile duct ligated rats; effect of pentobarbital sodium. AM Journal fisiol. 1986; 251:176-180; Nakano S., Harakane J. and Hashimoto H., Alteration in peribiliary ducts microcirculation in rats after common bile duct ligation. Hepatology, 1995, Vol. 21, No. 5: 1380-1995; Dumas Walla R., Belcowitz D., and H. Eubi J E. Adaptive response of the Enterohepatic circulation of bile acid to extra hepatic. Cholestiasis Hepatology 1996, Vol. 23, No. 3: 623-629 and Poo J. L., Stanes A., Pedraza-Chaverri J., Cruz C., Pérez C., Huberman A. and Uribe M: Cronologia de la Hipertensión Portal, Disminución de la Excreción de sodio y activación del sistema renina-angiotensina en cirrosis biliar experimental. Rev., Invest Clin, 49:15-23, 1997).

Ad5 gal was administered at the same time and from the same lot to control rats without cirrhosis. Rats with 5 and 8 weeks of $CCl_4$ intoxication and rats with 2 and 4 weeks of bile duct ligation (BDL) were sacrificed 72 hrs after administration of recombinant adenovirus for the histological analysis and determination of the expression of the galactosidase protein (gal) encoded by the AdR. For this purpose liver, spleen, heart, lungs, kidneys and brain were extracted, tissue sections were cut in cube shapes of 5 to 6 mm., which were absorbed in freeze medium Tissue-Tek O.C.T., the tissues were frozen at −30° C. and they were cut with a cryostat to obtain 8 µm sections These sections were placed on silanized glass slides and fixed with formaline, pH 8.5, during 15-30 minutes and were exposed to Xgal for 16-18 hours, being counterstained with Neutral Red stain. (Weiss D J. Ligitt D. and Clark J G. In situ Hiti Chemical Detection of galactosidase activity in lung: assessment of Xgal reagent in distinguishing 1AC-Z Gene expression and endogenous galactosidase activity. Human Gene Therapy, Sep. 1, 1997, 8:1545-1554). The percentage of positive cells was determined by morphometric analysis in multiple fields of the same size and calculating the average. Besides, liver sections of cirrhotic rats were obtained and tissues absorbed in paraffin were cut and stained with Sirius red which specifically stains collagenic proteins (Armendariz-Borunda J., and Rojkind M., A simple quantitative method for collagen typing in tissue samples: Its application to Human liver with schistosomiasis. Collagen Rel. Res 1984, Vol. 4, 35-47). Through this technique we can verify clearly the degree of fibrosis and the increase of bile ducts in the hepatic parenchyma. To verify the in vivo transduction of cells with GFP, we used healthy Wistar rats that received pAdGFP-MMP-8 vector. 72 hours later, a laparotomy was performed and the exposed organs were visualised in the microscope of fluorescence, closing the wound afterwards to keep the animal alive.

Figure 6:
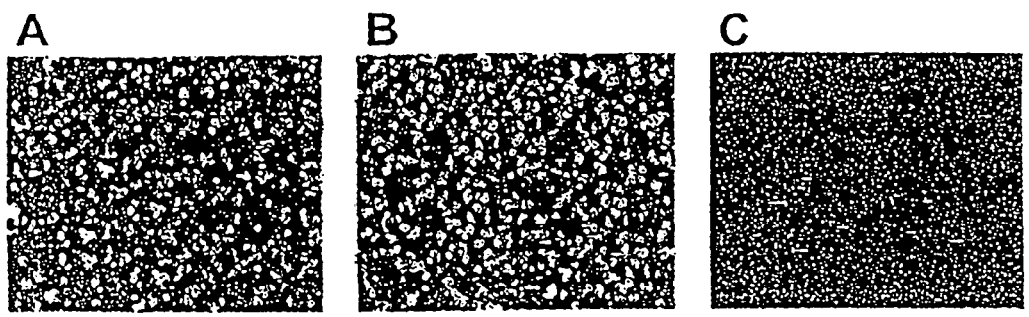
FIG. 6 shows the expression determination of green fluorescent protein (GFP) expression in cultured cells.

The previous results that are presented here regarding the study of the physiopathology of experimental hepatic cirrhosis are summarized in FIG. 2. Said figure shows the role of pro-inflammatory and pro-fibrogenic cytokines produced in vivo by Kupffer cells which, in turn, activate the hepatic stellate cells (HSC) to have them produce excess collagens deposited in the subendothelial space, obstructing the exchange between hepatocytes and sinusoids (Armendariz-Borunda J., Katayama K., and Seyer J. M.: Transcriptional mechanisms of type I collagen gene expression are differentially regulated by IL-1beta, TNFalfa and TGF into cells. J. Biol. Chem. 267:14316-14321, 1992; Armendariz-Borunda J., Katai H., Jones C. M. Seyer J. M. Kang A. H. and Raghow R.: Transforming growth factor beta is transiently enhanced at a critical stage during liver regeneration following CCL4 treatment. Laboratory Investigation. 69:283294, 1993 and Armendariz-Borunda J., Roy N., Simjewish C., Raghow R. Seyer J. M. and Kang A. H.; activation of Ito cells involves regulation of API collagen Gene Expression. Biochemical Journal 304:817-824, 1994). The degree of incorporation of Lac-z gene in cultured cells showed visible differences between techniques of Calcium-Phosphate, DNA-polylysine-lactose complexes and with the recombinant adenoviral vector in HepG2 and PMM (Peritoneal mouse macrophages). The degree of transduction with adenovirus reaches 100% and with the other two techniques about 1% as shown in FIG. 5. FIG. 6 shows the expression of green fluorescent protein (GFP) in cultured cells. A). Peritoneal mouse Macrophage transduced with the adenoviral vector pAdGFP-MMP8, 72 hours after its administration (50×), B). HepG2 cells transduced with the adenoviral vector pAdGFP-MMP8, 72 hours after its administration (50×) and C). HepG2 cells without the adenoviral vector. All the pictures were taken in a microscope stereoscope of fluorescence. It is necessary to point out that in the development to identify galactosidase activity, the cells must be fixed and they die. In the GFP assay, the cells are still intact and alive.

Figure 7:
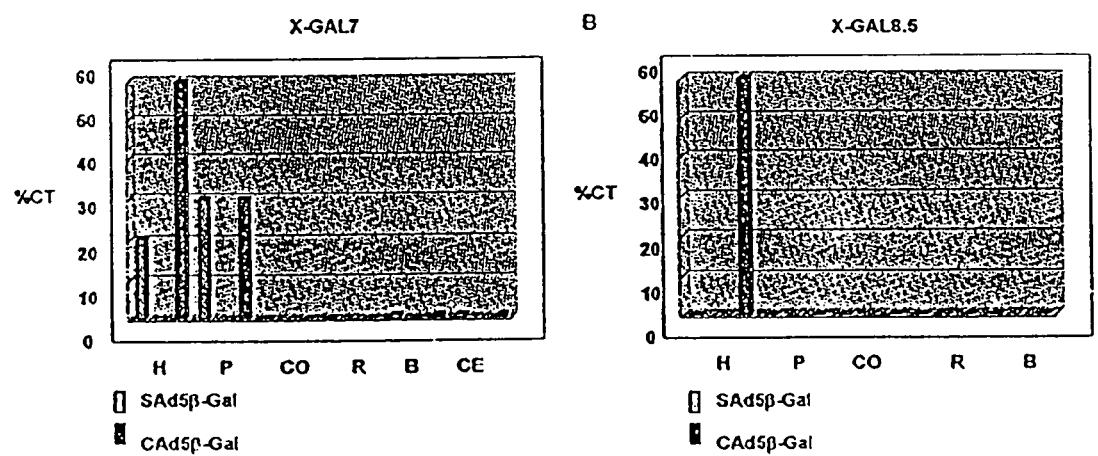
FIG. 7 shows the expression of -galactosidase in different organs after the infusion with Ad5 gal through the iliac vein.
Figure 8:
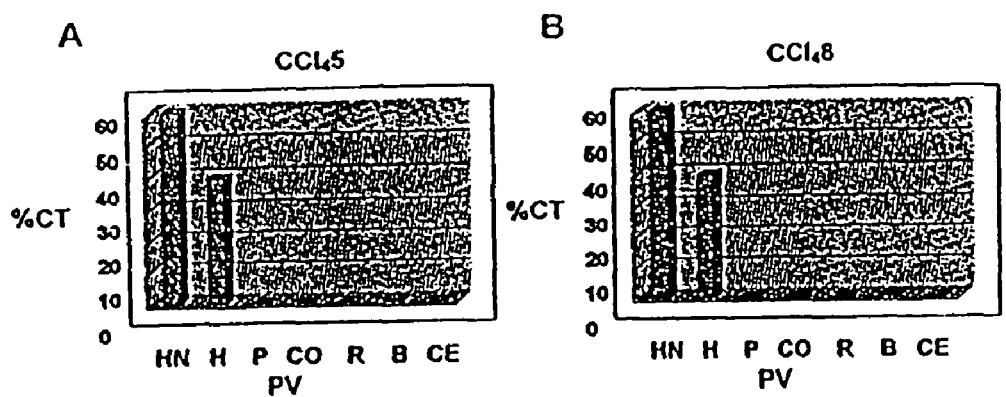
FIG. 8 shows the analysis of the tropism of the vector Ad5-gal to different organs of cirrhotic experiment animals by chronic intoxication with $CCl_4$, demonstrating that the main target organ is the liver.
Figure 9:
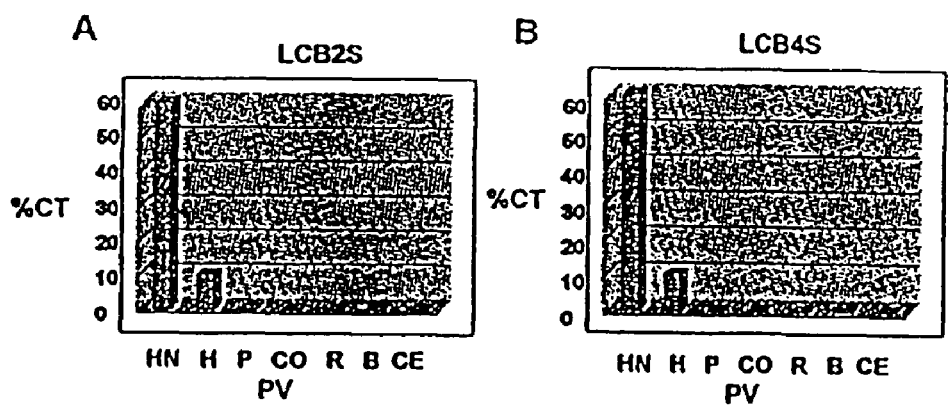
FIG. 9 shows the analysis of the tropism of vector Ad5-gal to different organs of cirrhotic experiment animals. Cirrhosis was induced by bile duct ligation and it was demonstrated that the main target organ is the liver.
Figure 10:
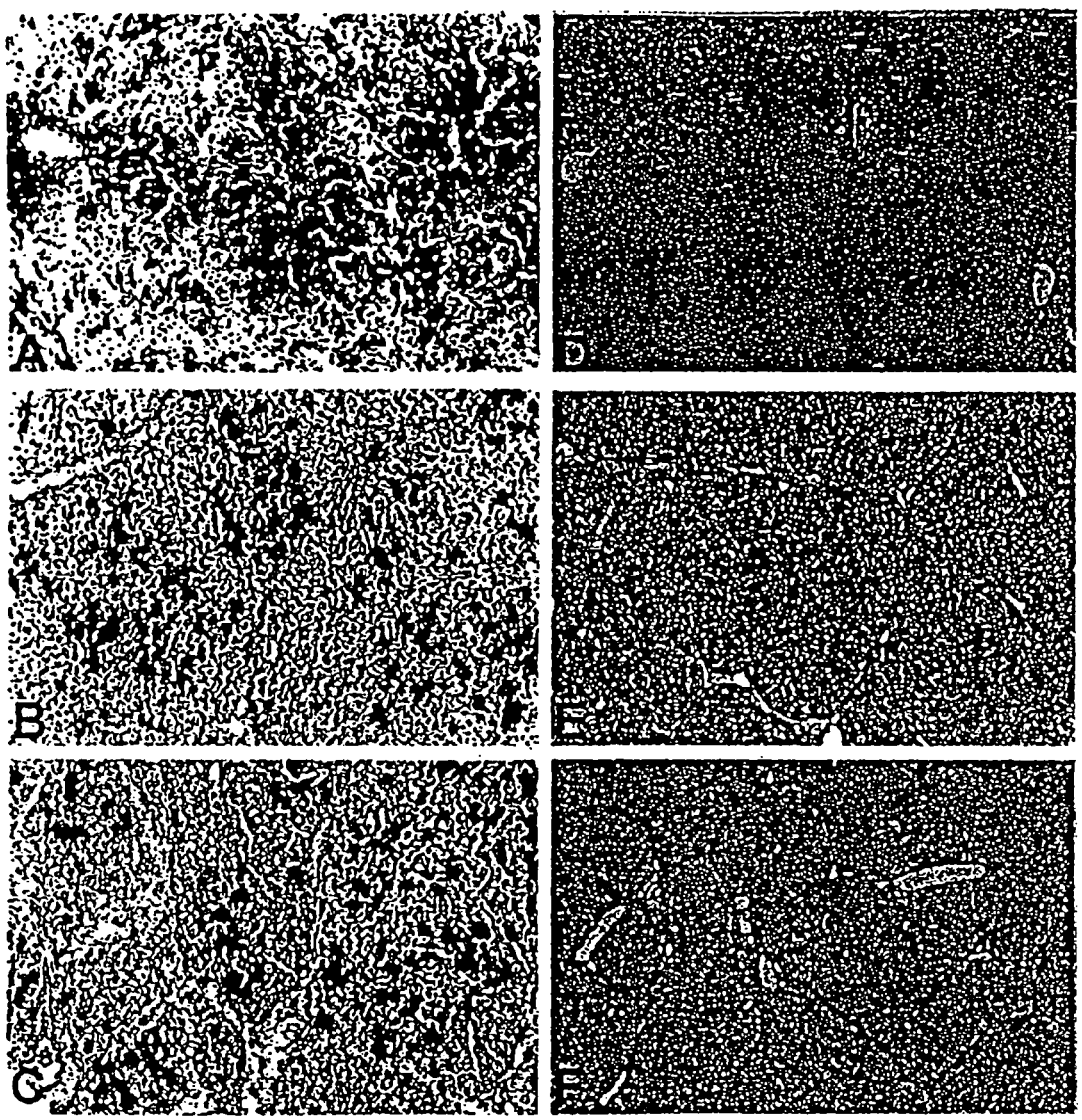
FIG. 10 shows histological sections of representative images of the in vivo efficiency transduction assays of the vector Ad5-gal in cirrhotic rats with chronic administration of $CCl_4$.
Figure 11:
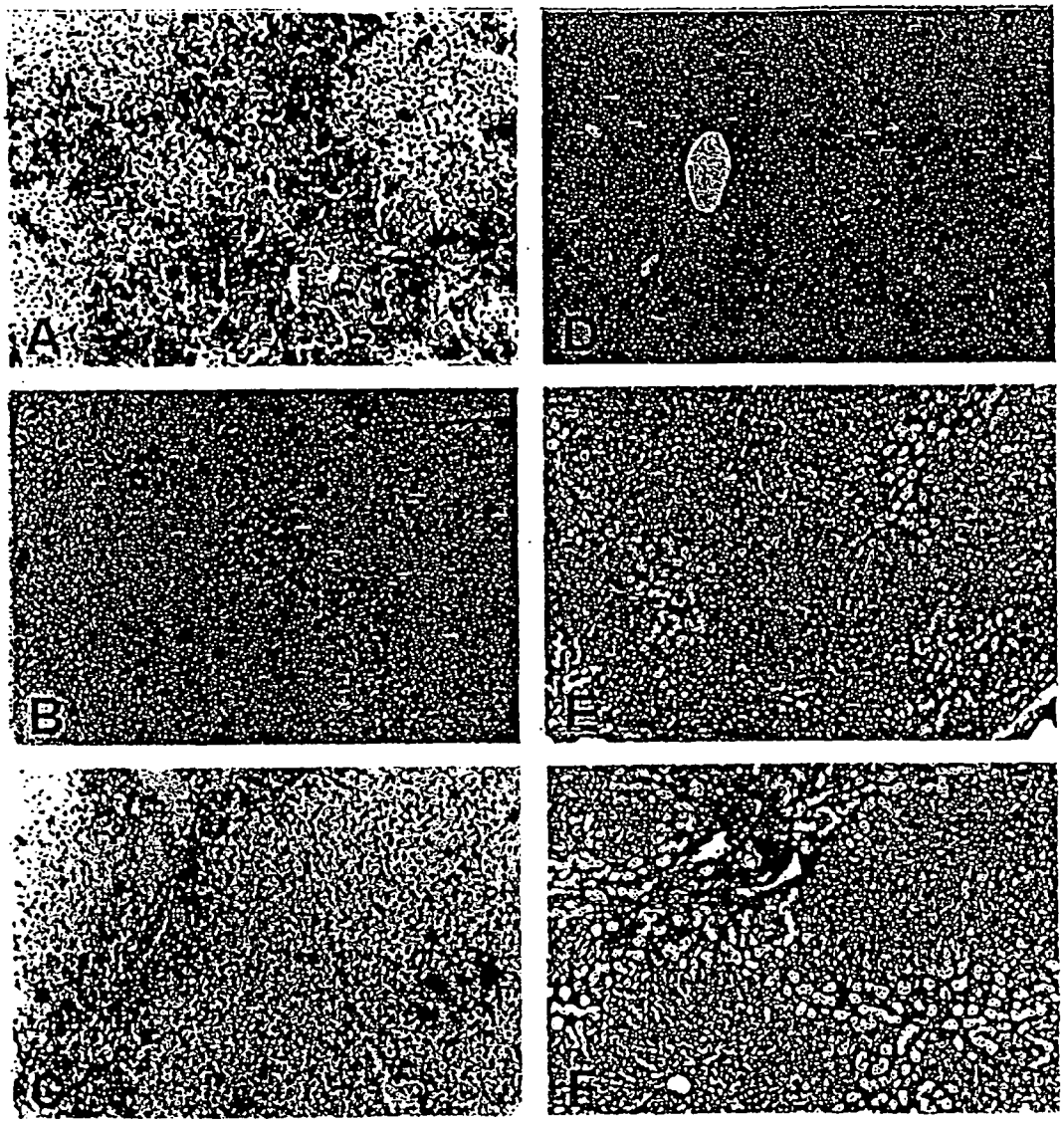
FIG. 11 shows histological sections of representative images of the in vivo efficiency transduction assays of the vector Ad5-gal in cirrhotic rats by common bile duct ligation.
Figure 12:
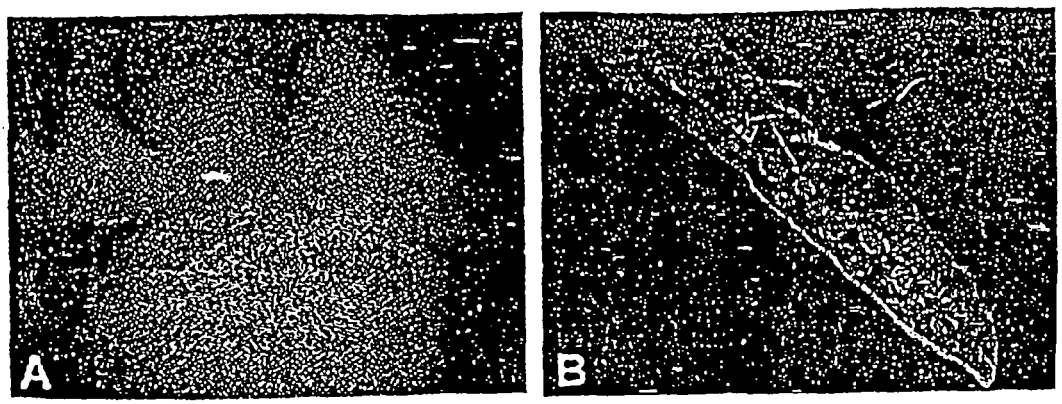
FIG. 12 shows the in vivo determination of the expression of the green fluorescent protein.

FIG. 7 shows the expression of gal in different organs after infusion with Ad5 gal by iliac vein. Fixation, washing and Xgal solutions using different pHs were used to discriminate among the endogenous expression and the bacterial exogenous galactosidase. In figure A, a pH 7.0 was used and in Figure B the pH was 8.5. This is the summary of the results of the assays of the different experimental conditions and it can be appreciated that the tissue exposition to Xgal solution with a pH 8.5 allowed us to eliminate the expression of endogenous galactosidase. We obtained frozen tissue sections from different organs: liver, kidney, lung, heart, brain and spleen from normal rats and intoxicated with $CCl_4$ for five and eight weeks. As represented in FIG. 8, the graphics show clearly that the main target organ is the liver, both in healthy rats as well as in rats with chronic administration of $CCl_4$. A) 5 weeks of $CCl_4$ administration and B) 8 weeks of $CCl_4$ administration. Spleen and lung present a degree of transduction below 1%, and thus this is not evident from the graphs. Rats received doses of $3\times10^{11}$ viral particles/ml of Ad5gal vector. The healthy control rats presented a total of 70% of hepatocytes transduced, while spleen and lung showed less than 1% transduction. In the other organs no transduction was found. Tissue sections were obtained from healthy rats as described before and compared with tissues from rats with 2 and 4 weeks of BDL. FIG. 9 clearly shows how the main target organ is the liver, both in healthy rats as well as in BDL rats. A) 2 weeks of LCB and B) 4 weeks of BDL. The spleen and the lung present a transduction grade lower than 1%, and thus it is hardly noticeable in graphs. With a dose of $3\times10^{11}$ viral particles/ml of the AD5gal vector, BDL rats present a total of 10% transduced hepatocytes. Besides liver, spleen and lung presented less than 1% transduction. The other organs showed no transduction. In FIG. 10, histological results are shown with the hepatic cirrhosis model induced by the chronic administration of $CCl_4$, where A) represents a liver section of a normal rat, 72 hours after the administration of Ad5 gal, by iliac vein (one representative cut of the experiments of a total of 5 rats). More than 70% of the hepatocytes are positive to the expression of gal (200×); D) The same liver as in Figure A, but stained with Sirius Red to observe collagen synthesis and deposition (200×); B) liver with 5 weeks of chronic intoxication with $CCl_4$. About 30-40% of the hepatocytes were successfully transduced; E). The same livers as in B, but stained with Sirius Red, the increase in the amount of collagen is notable and the liver architecture begins to distort (200×); C) rat liver after 8 weeks of chronic intoxication with $CCl_4$ to cause cirrhosis, again more than 40% of liver cells were positive for βgal expression and F) the same livers as in C, but stained with Sirius Red. Large deposits of collagen formed between the central and portal veins (200×) are characteristic. In FIG. 11, results obtained in the model of biliary duct ligation (BDL) induced cirrhosis are shown. A) shows a liver section of a normal rat 72 hours after the administration of Ad5 gal, by iliac vein (one representative cut of the experiments of a total of 5 rats). More than 70% of the hepatocytes are positive to the expression of gal (200×); D) the same liver as in Figure A, but stained with Sirius Red to observe collagen (200×); B) rat liver after 2 weeks of BDL. β-gal essay was conducted 72 hours after Ad5βGal administration, via iliac vein. About 10% of the hepatocytes were successfully transduced with the reporter gen; E) the same livers as in B, but stained with Sirius Red. Liver architecture begins to distort due to colestasis-induced fibrosis as well as to the important increase of biliar ducts (200×); C) rat liver after 4 weeks of BDL to cause cirrhosis. β-gal essay was conducted 72 hours after the administration of Ad5βGal, via iliac vein. Again, 10% of hepatocytes were successfully transduced and F) the same livers as in C, but stained with Sirius Red. Observe the large deposit of collagen proteins formed as well as the proliferation of biliar ducts (200×). FIG. 12 shows a laparotomy of a healthy Wistar rat that received pAdGFP-MMP-8 vector. The expression of the GFP is clearly seen in the liver and in insignificant amounts in the spleen. A very important fact is that the injection of adenoviral vectors did not induce lethal toxicity in experiment animals, both healthy and controls.

The preferred way to apply the present invention is through endovenous administration of the recombinant adenoviral vectors of this invention or the pharmaceutical compound which contains them, in which therapeutically effective amount is administered with an unitary dose regimen convenient to an individual with fibrosis. This regimen can be adjusted according to the affliction degree. Generally, unitary doses of about $10^7$ to $10^{14}$ viral particles for individual are employed. The preparation of a pharmaceutical compound including the adenoviral recombinant vectors of this invention can be conducted through the employment of standard techniques very well known by the persons skilled in the art, in combination with any of the pharmaceutically acceptable carriers described in the state of the art, including without limitation, starch, glucose, lactose, saccharose, gel, malt, rice, wheat flour, chalk, silica-gel, magnesium stearate, sodium stearate, powder of glyceril monostearate, NaCl, glycerol, propylene glycol, water, ethanol, and similar. These compounds can take the pharmaceutical form of solutions, suspensions, pills, tablets, capsules, powders and slow release formula, and similar.

The above description and the following examples have the purpose to illustrate particular embodiments of the invention and they should not be considered as limitations of the scope of this patent.

EXAMPLES

Example 1

Methodology to Demonstrate the Activity of Metalloprotease or Collagenase (MMP-8) and How to Regulate its Function a) Cell culture. HepG2 cells is a cell line of parenchymal origin derived from a human hepatoma, and were cultured in 60 mm culture dish, 37° C. in a wet atmosphere, with 95% air and $CO_2$ 5% atmosphere in Eagle's medium modified by Dulbecco (DMEM), supplemented with 10% fetal bovine serum, 2 mM L-Glutamax and antibiotics (100 U/ml penicillin and 100 g./ml. streptomycin).

b) Vectors of Expression of Latent and Active MMP-8 Genes

Figure 13:
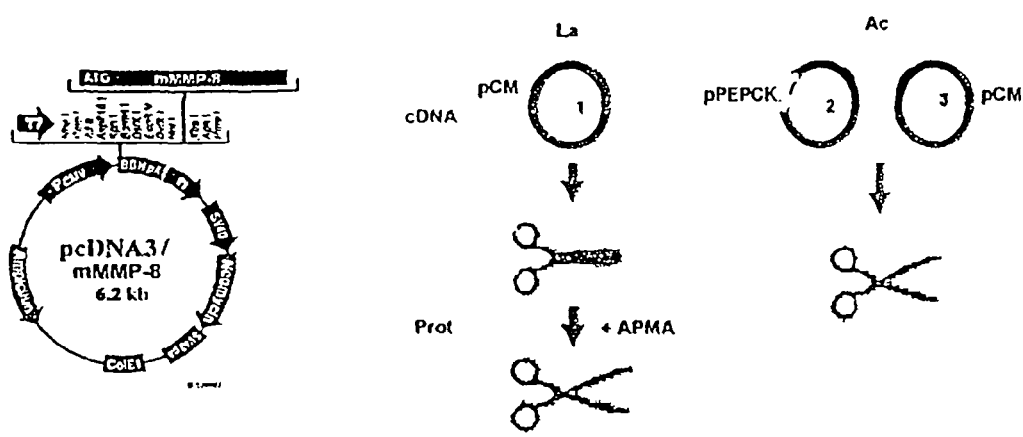
FIG. 13 shows the cloning strategy of the latent MMP-8 and active MMP-8.

Two plasmids were used with 2 kinds of MMP-8 genes to transfect the hepatic cells: The plasmid pcDNA-MMP-8 which contains the cDNA which encodes for latent MMP-8 (pro-MMP-8) together with the strong viral promoter of cytomegalovirus (CMV) (ATCC Deposit No. PTA 10532); and the plasmid pcDNA3MMP-8 containing the cDNA which encodes for the active MMP-8, together with the CMV promoter. This last one was created through subclonation using pcDNA3 and PETIIa-HNC plasmids, cutting with the restriction enzymes BamHI and XbaI and inserting the PCR product coding for the MMP-8 catalytic domain (which lacks the propeptide and carboxi-terminal fragments), as shown in FIG. 13, the delivery of latent and active MMP-8 genes. Two types of plasmids with the MMP-8 gene were used to be delivered to hepatic cells in culture: 1) PcDNA3-MMP-8, plasmid with the strong viral promoter of the cytomegalovirus (CMV) and the cDNA which encodes for the collagenase in its active form.

As a reporter gene $pSV_2$-gal plasmid was used. Said plasmid has the gene which encodes the enzyme -galactosidase inserted adjacent to the SV40 virus promoter.

c) Plasmid Transformation, Amplification and Purification

To obtain a large enough quantity of each one of the plasmids to be used in the various assays, each plasmid was introduced to *E. coli* DH5™, (this process is known as transformation), according to the instructions of the supplier. (Life Technologies, Gaithersburg, Md.): in a reaction tube 50 l of the competent strain DH5 were used and 2 l of plasmids (1-10 ng of DNA) were added. After mixing, it was incubated on ice during 30 minutes, a thermal shock (37° C. for 20 seconds) was applied and it was immediately chilled on ice for 2 minutes. At the end of this period of time, 0.95 ml of the bacterial culture medium Luria Base (LB) was added and it was stirred at 225 rpm during one hour to 37° C. to allow plasmid expression. After the expression, 50 l of the reaction mix were taken and seeded onto an Agar plate with 100 g/ml of ampiciline and it was incubated to 37° C. overnight. The colonies that grow after this period are those which contain the plasmid of interest, because of the resistance against the antibiotic.

To amplify the plasmid, two colonies were taken from the Agar plate and grown in a liter of LB medium containing 100 g./ml of ampiciline during 24 hours at 37° C., with constant stirring at 225 rpm. Once the optic density of the culture was 0.6, it is centrifuged to 6,000 rpm for 20 minutes to recollect the bacterial pellet. From this bacterial pellet, plasmidic DNA was separated from the genomic DNA of the bacteria using a kit of plasmids purification (Monster-prep, BIO101, Vista, Calif.), which is based on the alkaline lysis of the bacterial wall, the liberation of the plasmid in its interior and the separation of this DNA through a particular resin. The quantification of the plasmidic DNA was performed measuring spectrophotometrically the resultant absorbance at $\lambda=260$ nm.

d) Transfection of Cultured Cells

One of the most commonly used methods to introduce genes to eucaryotic cells, is DNA transfection with calcium phosphate, in which the exogenous DNA is precipitated as a fine complex on the cell surface, to be later incorporated by the cell and transiently integrated in the chromosomal DNA. To deliver the DNA with more selectivity to the hepatic cells, DNA is used in the form of complex with polylysine-lactose, because of hepatic cells have a specific receptor for Galactose in their cell membrane. For this, HepG2 cells were cultured at 70-80% confluence and then transfected with plasmids pcDNA-MMP-8, $pcDNA_3$-MMP-8 and $pSV_2$-galactosidase. Transfection was carried out by DNA precipitation with calcium phosphate (Graham, and Van derEb, 1973; Chen and Okayama 1988) and by complex formation with polylysine-lactose (Martinez-Fong et al, 1994). Briefly, cultured cells were added with the newly formed precipitate, product of the addition to plasmidic DNA of a solution of DNA with $CaCl_2$ 2M, in buffer solution HEPES pH 7.12 in case of the transfection with calcium phosphate or DNA complex with polylysine-lactose is added. Cells are incubated from 4-16 hours to allow the precipitate to appear to the cell surface, and later the DNA can be endocyted and introduced transiently to the nucleus. At the end of this time, the culture medium is replaced for a fresh one, see FIG. 14, where HepG2 cells are cultured with DMEM medium with 10% bovine fetal serum. When 60-80% confluency is reached, 10 mg of plasmid with MMP-8 gen is added in its latent form, as well as in the active or mature form. At the same time, the prokaryotic gene of galactosidase (-gal), is added to monitor the transfection and expression efficiency. MMP-8 gene was sent in different forms: naked, in complex with $CaPO_4$ or in complex with polylysine-lactose.

e) Formation of Complexes Polylysine-Lactose and DNA: Polylysine-Lactose (DNA:PL)

Figure 14:
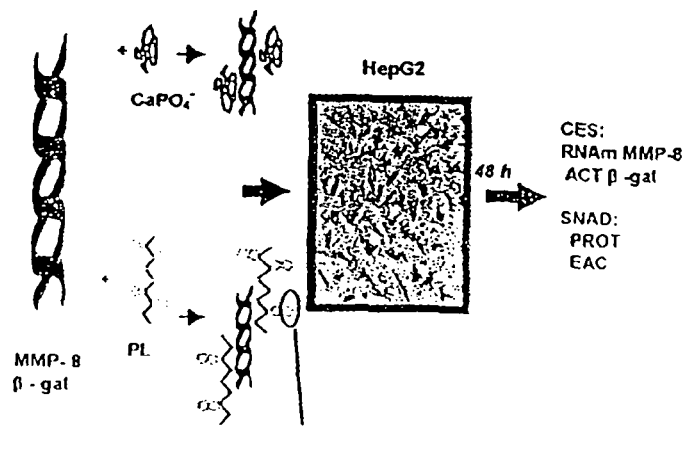
FIG. 14 shows the mechanisms of complex formation with DNA of MMP-8s for in vitro transfection essays in cells of hepatic origin (HepG2)
Figure 16:
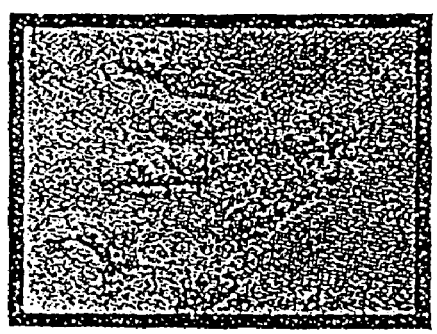
FIG. 16 shows the transfection efficiency in HepG2 cells (Cells of hepatic origin) with the plasmids of -galactosidase and cDNA-MMP-8.
Figure 16:
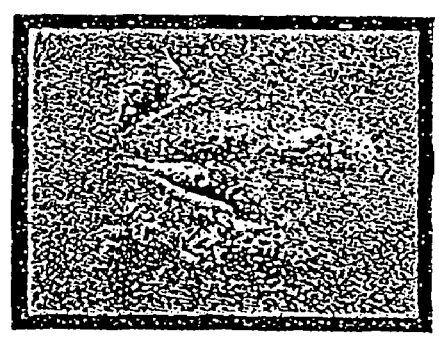
Figure 16:
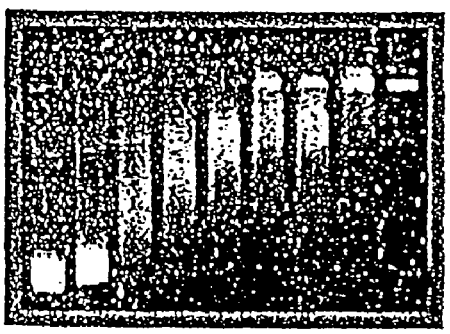
Figure 16:

The polylysine-lactose complex is formed when 14.8 mg of poly-L-Lysine (0.1 N) react with 200 l of -lactose 0.5 N (lactose-polylysine ratio: 1.0 N). Then, 20 mg of reducing agent sodium cyanoborohydride 3 M is added and it is incubated at 37° C. for 48 hours with constant stirring at 225 rpm. Then, the reaction goes through a desalting column (BioRad 10-DG) previously conditioned with phosphate buffer (PBS pH 7.2), which is eluted with the same buffer. Carbohydrate content is determined to the eluted fractions by the method of DuBois (1956) to analyze the degree of lactosylation of the complex and the contents of polylysine according the method of Shen et. al. (1984), which is considered as a base to evaluate the final concentration of the PL complex. The fraction with a major concentration of PL is used for its further reaction with the DNA of the plasmid containing the gene of interest, as is shown in FIGS. 14 and 16.

To evaluate the optimal molar ratio of DNA:PL to be used in transfection assays, the DNA was made to react with several concentrations of PL. At the end of one hour of incubation, samples were applied to a 1% retardation agarose gel and submitted to electrophoresis of DNA (60 millivoltios, 1.5 h), in which the DNA:PL complex with the largest PL contents runs a shorter distance than the one run by the free plasmid (0% retardation). The DNA:PL ratio which causes 80 to 90% of retardation of migration in the agarose gel was used as shown in FIG. 16 to obtain an efficient expression of exogenous genes of -galactosidase and pcDNA-MMP-8 delivered to HepG2 cells in complexes with $CaPO_4$ and polylysine-lactose.

f). Assays of Transient Expression Using the Reporter gen System of -Galactosidase (gal)

This system determines the activity of the -galactosidase enzyme as a measure of the level of expression of the transfected gene of interest along with Lac Z gene which encodes for this enzyme. The galactosidase is a bacterial enzyme which catalyzes the conversion of the uncolored substrate X-gal to a product of blue coloration. Because of this, the -galactosidase activity observed in eucaryotic cells subjected to transfection will indicate the successful incorporation of the gene of interest associated to the bacterial gene.

The assay of -gal for the stain of cells in culture dish consists in the fixation of cells at 4° C. during 5 minutes with 2% p-formaldehyde, the subsequent wash with PBS (3x) and the addition of one ml of a stain solution in PBS containing 20 mM potassium ferricianide, 20 mM potassium ferrocianide and 2 mM Magnesium Chloride followed by the addition of the substrate Xgal in a final concentration of 0.5 mg/ml. After incubation at 4° C. overnight (18 hours) blue cells are identified under the microscope (Ausubel, 1995).

g) RNA Extraction 48 hours after transfection, cells are recollected to extract RNA by the Method of Chomczynski and Sacchi (1987) using the reactive of Trizol™, as described hereinafter: to each one of the cell dishes one ml of PBS solution was added and cells were recollected by scraping them from the dish and transferred to an Eppendorf tube. It was then centrifuged at 1000 rpm for one minute and the cell pellet was treated with 500 l of Trizol, homogenized and incubated for 5 minutes at 4° C. One hundred μl of chloroform were added, and incubation was conducted during 5 minutes at 4° C. After this, it was centrifuged at 12,000 g for 15 minutes at 4° C. and the aqueous upper phase was transferred to a clean tube in which an equal volume of isopropanol is added and incubated at −70° C. during 15 minutes to precipitate the extracted RNA. Then, it is centrifuged at 12,000 g during 15 minutes at 4° C., the supernatant is eliminated through decantation and drying the tube with clean and sterile paper. Then, 500 l of 75% ethanol were added and it was centrifuged at 12,000 g during 10 minutes to 40° C. Finally, the RNA pellet was resuspended with 20 to 50 l of deionized water treated with diethylpirocarbonate (DEPC) and RNA concentration was quantified by spectrophotometry at $\lambda=260$ nm.

h) Analysis of Expression of MMP-8 Gene by the Polymerase Chain Reaction (PCR) Associated to the Reaction of Reverse Transcriptase (RT-PCR).

To determine the degree of expression of the exogenous gene of MMP-8 incorporated to the cell, complementary DNA was obtained (cDNA) starting from RNA previously extracted and then amplifying the expression signal by the Polymerase Chain Reaction.

To obtain the cDNA, the following procedure was used: 2 g of total RNA were taken to a volume of 8 l with deionized, sterilized water and incubated at −70° C. for 10 minutes. Then, the sample was stirred in iced water during 5 minutes and still in the ice, the following reagents were added: 4 l of 5× buffer for the RT enzyme, 4 l dNTP's mix 2.5 mM, 1 l random primers (1 g/l), 1 l inhibitor of RNAase (one U/l) and finally 2 l of the Reverse Transcriptase enzyme (200 U/l). The reaction mix was incubated at room temperature for 10 minutes and then at 37° C. for one hour. At the end of this time, it was placed immediately in a temperature of 95° C. for 10 minutes, and then it was placed on iced water during 5 minutes with constant stirring and it was stored at −70° C. until its further use.

To analyze the specific expression of MMP-8 gen, a PCR reaction was set up using the primers or oligonucleotides specific for this gene according to the experimental conditions described hereinafter: in a reaction tube containing 2 l of cDNA 5 l of 2.5 mM $MgCL_2$, 5 l 5× buffer for the polimerase enzyme, from leukemia murine virus moloney (MMLV), 1 of 2.5 mM dTNPs, 5 l of the sense primer 3 μM, 5 l of the antisense primer 3 μM, 1 l of the polymerase enzyme (U/l) and it is taken to a final volume of 50 l with deionized water (Innis et al. 1990). The oligonucleotide sense primer specific for MMP-8 is 5'-AGCTGTCAGAGGCTGGAGGTAGAAA-3' (SEQ. ID 1), and the antisense primer is 5'-CCTGAAAG-CATAGTTGGGATACAT-3'(SEQ. ID 2) (Cole et al. 1996). After the addition of these reagents, the mix was placed in a thermalcycler during 30 cycles according to the following program: denaturation (94° C., 5 min), annealing (60° C., 1 min) and extension (72° C., 1.5 min). Then, PCR products are submitted to electrophoresis (60 mV, 1.5 h) in a 1.5% agarose gel.

i) Assay of Collagenase Activity.

The analysis of enzymatic activity of collagenase was performed to determine the functionality of the enzyme produced, because this protein could be found enzymatically inactive, even when RNA expression was positive. Cells are cultured in serum-free medium for 24 hours, culture medium is recollected and activity of collagenase secreted by the cells is determined by a modified method of Hasty et al. (1986) to identify products of degradation of specific collagen substrate through 8% polyacrylamide gel electrophoresis.

Briefly: cell supernatants containing 1-1.5 gr of protein were incubated at 27° C. during 18 hours with 5 g of native collagen type I and 60 l of the incubation buffer: 50 mM Tris-HCl, 5 mM $CaCl_2$, 0.02% $NaN_3$, 50 mM arginine, 1% Triton X-100 and in absence or presence of 1 mM APMA, pH 7.6. Finally, 30 l of product of reaction were mixed with 30 l of sample buffer for proteins and electrophoresis in SDS-polyacrylamide gels (7.5%) was run to identify the degradation products $1^A$ and $2^A$ of collagen type 1.

Example 2

Figure 15:
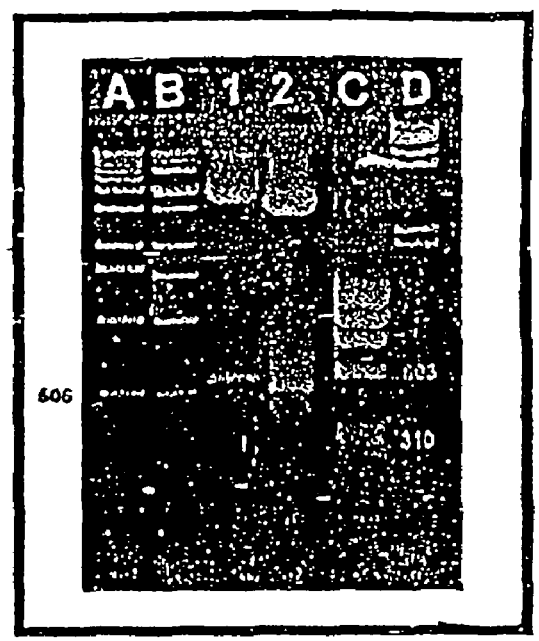
FIG. 15 shows the verification through electrophoresis in agarose gels of the success of cloning of MMP-8 cDNAs in the appropriate plasmids.

Results to Demonstrate the Activity of Metalloprotease or Collagenase (MMP-8) and Therefore to Regulate its Function Subcloning permitted to incorporate MMP-8 cDNA encoding for the fully functional enzyme was subcloned in a vector appropriate to our needs. Thus, FIG. 15 shows an electrophoresis of the DNA fragments released by cutting MMP-8 plasmids with restriction enzymes. Lane A). Marker of bp of 1 Kb DNA ladder (Gibco BRL); B). Perfect DNA marker (Novagen, Inc.); 1) pcDNA-MMP-8 cutting with BamHI and XbaI; 2) pcDNA3-MMP-8 cutting with BamHI and XbaI; C) φX174 marker (Gibco BRL); λ Hind III Marker (Gibco BRL), in which the latent MMP-8 cDNA (lane 1) and the mature MMP (lane 2); were successfully subcloned in the expression vectors pcDNA and pcDNA3. The released inserts are observed after treatment with restriction enzymes BamHI and XbaI. The bands stained with ethidium bromide correspond to each of cDNA (between 506 and 560 base pairs) for mature and latent MMP-8 cDNA, respectively. To evaluate the efficiency of incorporation of the cDNA for MMP-8 delivered to HepG2 cells in form of complex with $CaPO_4$ and with polylysine-lactose, the co-transfection of this plasmid was realized along with the reporter gene of -galactosidase. In this way, cells observed in the microscope with blue staining, indicate indirectly that they have also incorporated to the plasmid of interest. FIG. 16 shows the expression of -galactosidase in HepG2 cells, co-transfected with free plasmid, in form of complex with $CaPO_4$, or in its form of complex with polylysine-lactose. This figure shows that the DNA binding with polylysine-lactose was accomplished because the higher the polylysine concentration, the clearer the retardation of -gal plasmid. The ratio selected to transfect the cells was the one that delayed 80% of plasmid migration.

Figure 17:
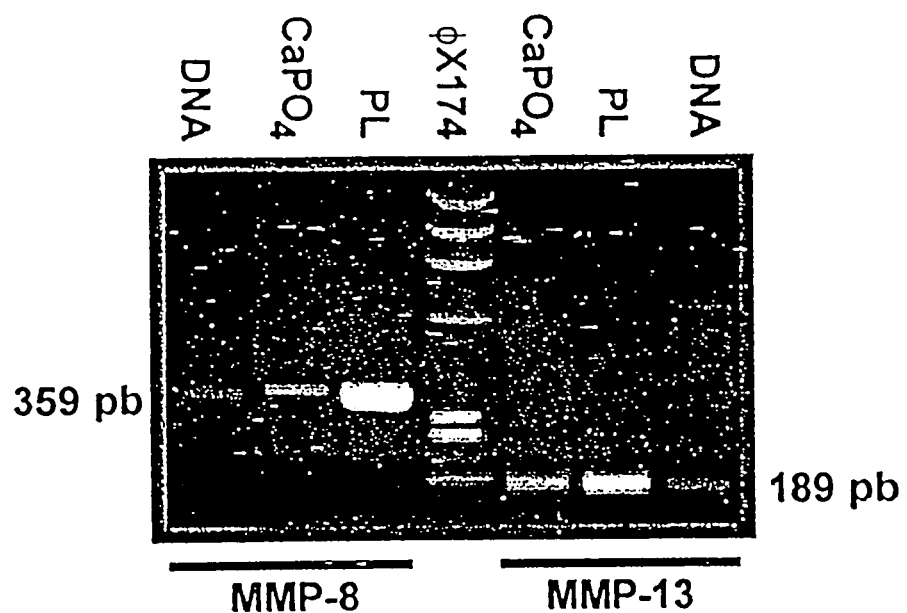
FIG. 17 shows the analysis by polymerase chain reaction associated to reverse transcriptase (RT-PCR) of MMP-8 messenger RNAs.

Once demonstrated that the cells in culture are capable of incorporate and express genes that have been transfected, it was necessary to corroborate that such genes were transcribed by the machinery of host cells by means of RT-PCR assays. FIG. 17 shows an analysis by RT-PCR of messenger RNA for MMP-8 and MMP-13. (This plasmid was used as a further positive control of transfection); in which a DNA electrophoresis of PCR amplified products, of the cDNA for MMP-8 delivered as a complex with $CaPO_4$ and polylysine-lactose, has been transcribed for both cases in transfected HepG2 cells. It is observed that product signal of PCR of MMP-8 (359 base pairs), was more intense when plasmid was delivered as a complex with polylysine-lactose.

To demonstrate that MMP-8 transcripts expressed by HepG2 cells was translated into a functional protein, the assay for enzymatic activity was conducted, using collagen type I as substrate. FIG. 18 shows the enzymatic activity of type I collagen degradation of the protein secreted in the culture medium, which was observed in the transfected cells with the gene of latent MMP-8. With previous activation with the mercurial agent APMA (lane 7) and with the gene of active MMP-8 complexed with $CaPO_4$ (lane 9) and with polylysine-lactose (lane 10), and its specific inhibition with EDTA 2 mM. Negative controls: type I collagen without addition of supernatants of cells (lane 1) and with addition of Trypsin (lane 3), collagen with supernatants of cells without transfection (lane 2). Positive controls: type I collagen with supernatant of human leukocytes (lane 3), type I collagen with addition of 0.015% bacterial collagenase (lane 4); and degradation products of native type I collagen, separated in a 6% polyacrylamide gel, after it was incubated with supernatant of transfected cells with latent and active MMP-8 genes. It was observed how in both cases the collagenolytic activity is clear in presence of APMA in the case of latent MMP-8, and its inhibition for EDTA for both latent and active MMP-8. This fact shows that this proteolytic activity corresponds to a metalloprotease of interstitial matrix. The incubation of native type I collagen with trypsin did not show degradation. So, this experiment clearly shows that MMP-8 action was specific considering the intact nature of the collagen molecule.

Figure 19:
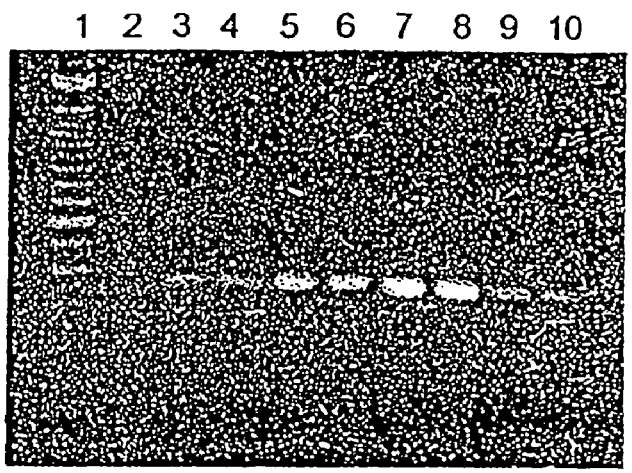
FIG. 19 shows the hormonal regulation of the MMP-8 gene expression under the transcriptional control of the regulable promoter PEPCK and, FIG. 20 shows the dose-response assay of the different doses used to determine the best response of "in vivo" hepatic transduction with the -galactosidase reporter gene.
Figure 20:
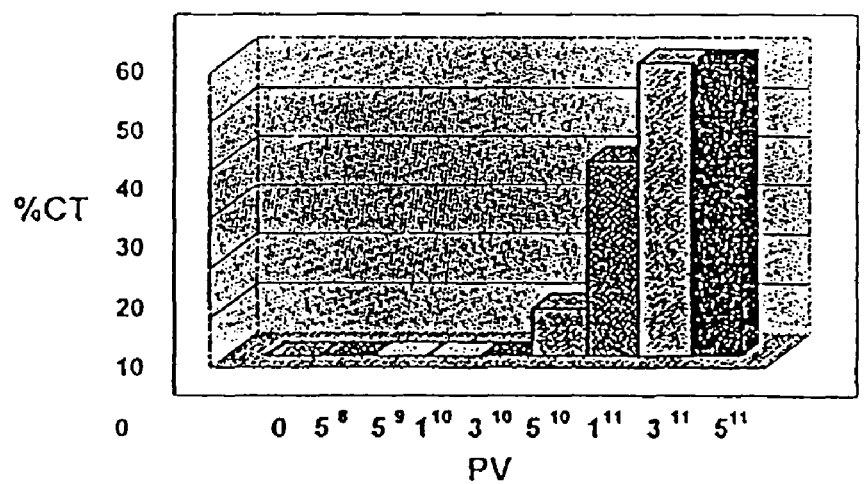

FIG. 19 shows evidence that activities of the enzymes that specifically degrade collagen can be controlled (turned off and/or turned on) through the cloning of its respective cDNAs that are themselves under the transcriptional control of promoters of regulable genes, such as the PEPCK (Phosphoenolpiruvate carboxykinase) gene. It is clear that both the stimulation of cells in culture with Glucagon (lanes 5 and 6), and cyclic AMP (lanes 7 and 8), up-regulate their production of messenger RNA that codes for MMP-8. It is also clear that insulin lowers said production (lanes 9 and 10).

The observations regarding the activity of endogenous -galactosidase suggest that this activity is usually granular and weaker in color than the dark blue as a result of the activity of exogenous enzyme (Shimohama S., Rosenbergh M B. Fagan A M, Wolff J A, Short M P, Bradfielf X O, Friedman T., and Gage F H: Genetically Modified Cells into the rat brain: Characteristics of *E. coli*-Galactosidase as a reporter gene. Brain Res. 5:271-278, 1989). Many modifications have been described to increase the specificity in the determination of exogenous Lac Z gene essay. Thus, according to previous information by Weiss, D J, Ligitt D., and Clark J G. In situ histochemical detection of beta-galactosidase activity in lung. Assessment of Xgal reagent in distinguishing Lac Z gene Expression and endogenous -galactosidase activity. Human Gene Therapy, Sep. 1, 1997, 8:1545-1554; in the present invention a solution of X-gal, with a pH 8.5 was used; in this way, the activity of exogenous -gal was demonstrated, minimizing the endogenous activity in vivo.

One of the indicators actually used for in vivo monitoring the efficiency and location of transduced cells with recombinant adenoviruses, is the detection of green fluorescent protein (GFP) expression. For this purpose, the gene which encodes for this protein is subcloned in adenoviral vectors, and then through the use of a fluorescent microscope, the fluorescence given by GFP can be observed directly without sacrificing the experiment animal which received the vector (Rojas-Martinez, A, Wyde P R, Montgomery Calif., Chen S H, Woo S L C and Aguilar-Cordova E.: Distribution toxicity and lack of replication of an E1A-recombinant adenoviral vector after systemic delivery in the cotton rat. Cancer Gene Ther. 1998, y TongChuan H., Shibin Z., Luis T., Jian Y., Kenneth W., and Vogelstein Berth: A simplified system for generating recombinant adenoviruses. Proc. Natl. Acad. Sci. USA Vol. 95:2509-2514, March 1998). A large body of data has been obtained that shows that, after the i.v. administration of adenoviruses in healthy animals, the main target cells were hepatocytes. This has been observed in mice, rabbits, dogs and primates (Zern A M. and Kresina T F, Hepatic drug delivery and gene Therapy. Hepatology 1997, vol. 25, No. 2, 484-491), but not in cirrhotic rats. Probably, the injection in portal vein could be more efficient to get to the target cells in the liver, providing them a favorable innoculum of viral particles to the entire liver before being diluted into the bloodstream. This route is efficient, but it has the disadvantage that it requires a laparotomy. On the other hand, peritoneal administration is a faster and simpler infusion, but it does not promote hepatocyte transduction. The results of the present invention show that the injection of $3\times10^{11}$ viral particles by iliac vein in normal Wistar rats of approximately 200 g. produces a very high level of expression (70% of transduced hepatocytes). Our results are consistent with a previous report in which specific delivery of reporter genes in primates by saphenous vein produced almost the same level of transduction and expression of the transgene in the liver, as compared with infusion through portal vein (Marie Jean T F D, Poeters V., Lieber A., Perkins J., and Kay M A. Methods for multiple portal vein infusion in mice: Quantitation of adenovirus-mediated hepatic gene transfer. Biotechniques February 1996, 20; 278-285 and Zhu G. Nicholson A G. Zheng X., Strom T B, and Sukhame V P. Adenovirus mediated -galactosidase gene delivery to the liver leads to protein deposition in kidney glomeruli. Kidney international, 1997, Vol. 52, 992-999). Furthermore, the expression of the reporter gene in our animals with cirrhosis induced by chronic administration of $CCl_4$ was surprisingly almost as high as the normal rats (40% of transduced hepatocytes). These results are very exciting because our cirrhotic animals could hardly survive the surgical procedure required to administrate the adenovirus by the portal vein. This is due to altered functional hepatic tests, and elevated prothrombin time as well as important bleeding. Although rats with bile duct ligation showed a substantial reduction in the number of transduced hepatocytes (5-10%), it is also important the number of hepatocytes, which eventually could be transduced with therapeutic genes, such as metalloproteases (MMP-8) and/or genes which encode for stimulating proteins for hepatic regeneration such as uPA (Urokinase Plasminogen Activator) and Smad 7.

Other embodiments will be evident for people skilled in the art based on the present description. Said embodiments are included within the true scope and spirit of the invention.

The definitions of the symbols used in the figures corresponding to the present invention, are shown below:

FIG. 1:

| | |
|---|---|
| CEH = | stellate hepatic cell. |
| CES = | Endothelial sinusoidal cell. |
| CK = | Kupffer Cell. |
| ESET = | Subendothelial space. |
| HE = | Hepatocytes. |
| HIDC = | Liver with chronic damage. |
| HN = | Normal liver |
| SINU = | Sinusoid |

-continued

FIG. 2:

| | |
|---|---|
| COLASA = | Collagenase |
| DCA = | Degradation of collagen. |
| TGE = | Experimental genic therapy |
| MMPs = | Metalloproteases |

FIG. 3:

| | |
|---|---|
| CT293 = | Co-transfection in cells 293 |
| PG CsCl = | Purification with CsCl gradients |

FIG. 4:

| | |
|---|---|
| BD = | Right arm. |
| BI = | Left arm. |
| CTBK = | Co-transfection in bacteria and selection in Kanamicine. |
| CUL = | Culture |
| LI PacI = | Linearize with Pac I. |
| LI PmeI = | Linearize with Pme I |
| PV = | Viral particles |
| T293 = | 293 Cell transfection |
| GENADR = | Generation of recombinant adenovirus. |

FIG. 7:

| | |
|---|---|
| B = | Spleen. |
| CE = | Brain |
| CO = | Heart |
| % CT = | Percent of transduced cells |
| H = | Liver |
| P = | Lung |
| R = | Kidney |
| Sad -gal = | Without the Ad -gal vector |
| CAD -gal = | With the Ad -gal vector |
| X-GAL7 = | Reactive X-gal, pH 7.0 |
| X-GAL 8.5 = | Reactive X-gal, pH 8.5 |

FIG. 8:

| | |
|---|---|
| B = | Spleen. |
| CCl45 = | 5 weeks of intoxication with CCL4 |
| CCl48 = | 8 weeks of intoxication with CCL4 |
| CE = | Brain |
| C0 = | Heart |
| % CT = | % of transduced cells |
| H = | Liver |
| P = | Lung |
| R = | Kidney |
| PV = | Viral particles |
| HN = | Normal Liver |

FIG. 9:

| | |
|---|---|
| B = | Spleen |
| CE = | Brain |
| CO = | Heart |
| % CT = | % of transduced cells |
| H = | Liver |
| LCB2S = | 2 weeks of bile duct ligature |
| LCB4S = | 4 weeks of bile duct ligature |
| P = | Lung |
| R = | Kidney |
| PV = | Viral particles |
| HN = | Normal Liver |

FIG. 13:

| | |
|---|---|
| PROT = | Protein |
| APMA: | MERCURIAL AMONOPHENYL ACETATE |

FIG. 14:

| | |
|---|---|
| ACT -gal = | - galactocidase activity |
| CES = | Cells |
| EAC = | Enzymatic Activity |
| PL = | Polylysine |
| PROT = | Protein |
| RGAL = | Galactose residues |
| SNAD = | Supernatant |

FIG. 16:

| | |
|---|---|
| ADND = | Naked DNA. |
| GELRADN-PL = | Retardation gel for polylysine |

FIG. 18:

| | |
|---|---|
| CA = | With APMA. |
| CACE = | With APMA and EDTA. |
| CaPO4 = | Phosphate. |
| CE = | With EDTA. |
| COB = | Bacterial Collagenase. |
| COL1 = | Type I Collagen |
| PL = | Polylysine |
| SA = | Without APMA |
| SNL = | Leucocyte Supernatant |
| ST = | No-transfected |
| TRIP = | Trypsin |

FIG. 20:

| | |
|---|---|
| % CT = | % of transduced cells. |
| PV = | Viral particles. |

The invention claimed is:

1. A method of delivering matrix metalloproteinase 8 (MMP-8) to the liver of a subject in need of delivery thereof, the method comprising delivering a composition by an intravenous administrative route to the subject, the composition comprising a pharmaceutically compatible carrier and unitary doses of viral particles of a recombinant adenoviral vector, wherein said unitary dose is from about $10^7$ to about $10^{14}$ viral particles and the adenoviral vector is the vector contained in ATCC Deposit No. PTA-10532.

* * * * *

SEQUENCE LISTING

```
<160> NUMBER OF SEQ ID NOS: 2

<210> SEQ ID NO 1
<211> LENGTH: 25
<212> TYPE: DNA
<213> ORGANISM: artificial
<220> FEATURE:
<223> OTHER INFORMATION: sense primer for MMP-8

<400> SEQUENCE: 1
agctgtcaga ggctggaggt agaaa                                           25

<210> SEQ ID NO 2
<211> LENGTH: 24
<212> TYPE: DNA
<213> ORGANISM: artificial
<220> FEATURE:
```

-continued

```
<223> OTHER INFORMATION: anti-sense primer for MMP-8

<400> SEQUENCE: 2
cctgaaagca tagttgggat acat                                              24
```